(12) United States Patent
Bernalier-Donadille et al.

(10) Patent No.: US 10,086,020 B2
(45) Date of Patent: *Oct. 2, 2018

(54) COMPOSITIONS COMPRISING BACTERIAL STRAINS

(71) Applicant: 4D PHARMA PLC, Leeds (GB)

(72) Inventors: Annick Bernalier-Donadille, La Roche Blanc (FR); Laureen Crouzet, Beaumont (FR); Chloe Habouzit, Chamalieres (FR)

(73) Assignee: 4D Pharma PLC (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/915,885

(22) Filed: Mar. 8, 2018

(65) Prior Publication Data

US 2018/0207207 A1 Jul. 26, 2018

Related U.S. Application Data

(63) Continuation of application No. PCT/GB2017/052077, filed on Jul. 13, 2017.

(30) Foreign Application Priority Data

| Jul. 13, 2016 | (GB) | 1612190.7 |
| Sep. 20, 2016 | (GB) | 1616016.0 |
| Sep. 20, 2016 | (GB) | 1616018.6 |
| Mar. 6, 2017 | (GB) | 1703548.6 |
| Mar. 6, 2017 | (GB) | 1703552.8 |

(51) Int. Cl.
| *A61K 9/00* | (2006.01) |
| *A61K 31/04* | (2006.01) |
| *A61K 9/19* | (2006.01) |
| *A61K 35/74* | (2015.01) |
| *A61P 1/12* | (2006.01) |
| *A61K 9/48* | (2006.01) |
| *A61P 1/10* | (2006.01) |
| *A61K 35/00* | (2006.01) |

(52) U.S. Cl.
CPC ............... *A61K 35/74* (2013.01); *A61K 9/19* (2013.01); *A61K 9/48* (2013.01); *A61P 1/10* (2018.01); *A61P 1/12* (2018.01); *A61K 2035/11* (2013.01)

(58) Field of Classification Search
CPC .......... A61K 2300/00; A61K 2039/505; A61K 31/194; A61K 31/215; A61K 31/708; A61K 2039/507; A61K 45/06; A61K 35/747; C07K 16/244; C07K 2317/76; C07K 2317/92; C07K 16/468; C07K 2317/33; C07K 2317/24; C07K 2317/31; C07K 2317/52; C07K 2317/55; C07K 2317/56; C07K 2317/565; C07K 2317/567; C07K 2317/622; C07K 2317/73; C07K 2319/30; C07K 14/47

See application file for complete search history.

(56) References Cited

U.S. PATENT DOCUMENTS

| 5,589,168 A | 12/1996 | Allen et al. |
| 6,348,452 B1 | 2/2002 | Brown et al. |
| 6,645,530 B1 | 11/2003 | Borody |
| 7,749,494 B2 | 7/2010 | Renaud et al. |
| 7,998,474 B2 | 8/2011 | Kelly |
| 8,460,648 B2 | 6/2013 | Borody |
| 9,011,834 B1 | 4/2015 | McKenzie et al. |
| 9,314,489 B2 | 4/2016 | Kelly et al. |
| 9,539,293 B2 | 1/2017 | Kelly et al. |
| 9,610,307 B2 | 4/2017 | Berry et al. |
| 9,662,381 B2 | 5/2017 | Honda et al. |
| 9,796,762 B2 | 10/2017 | Kelly et al. |
| 9,808,519 B2 | 11/2017 | Honda et al. |
| 9,839,655 B2 | 12/2017 | Mulder et al. |
| 2003/0147858 A1 | 8/2003 | Renaud et al. |
| 2008/0069861 A1 | 3/2008 | Brown et al. |
| 2010/0247489 A1 | 9/2010 | Saur-Brosch |
| 2010/0284973 A1 | 11/2010 | Schiffer-Mannioui et al. |
| 2010/0303782 A1 | 12/2010 | Cobb et al. |
| 2010/0311686 A1 | 12/2010 | Kasper et al. |
| 2010/0316617 A1* | 12/2010 | Renaud ............... A61K 35/742 424/93.41 |
| 2014/0037716 A1 | 2/2014 | Nowill et al. |
| 2014/0147425 A1 | 5/2014 | Henn et al. |
| 2014/0154218 A1 | 6/2014 | Kohno et al. |
| 2014/0199281 A1 | 7/2014 | Henn et al. |
| 2014/0335131 A1 | 11/2014 | Mazmanian et al. |
| 2014/0341921 A1 | 11/2014 | Honda et al. |
| 2015/0071957 A1 | 3/2015 | Kelly et al. |
| 2015/0104418 A1 | 4/2015 | Flint et al. |
| 2016/0067188 A1 | 3/2016 | Cade et al. |
| 2016/0184370 A1 | 6/2016 | McKenzie et al. |
| 2016/0199424 A1 | 7/2016 | Berry et al. |
| 2016/0279177 A1 | 9/2016 | Kelly et al. |
| 2017/0143772 A1 | 5/2017 | Mulder et al. |

(Continued)

FOREIGN PATENT DOCUMENTS

| CN | 101590081 A | 12/2009 |
| CN | 102940652 A | 2/2013 |

(Continued)

OTHER PUBLICATIONS

Distrutti, et al., Hydrogen sulphide induces u opioid receptor-dependent analgesia in a rodent model of visceral pain. Molecular Pain, 2010; 6(36):1-16.

(Continued)

*Primary Examiner* — Padmavathi Baskar

(74) *Attorney, Agent, or Firm* — Wilson Sonsini Goodrich & Rosati

(57) ABSTRACT

The invention provides compositions comprising one or more bacterial strains for treating preventing diarrhea and/or constipation.

11 Claims, 5 Drawing Sheets

Specification includes a Sequence Listing.

(56) References Cited

U.S. PATENT DOCUMENTS

| | | |
|---|---|---|
| 2017/0143773 A1 | 5/2017 | Mulder et al. |
| 2017/0143774 A1 | 5/2017 | Mulder et al. |
| 2017/0143775 A1 | 5/2017 | Mulder et al. |
| 2017/0173089 A1 | 6/2017 | Kelly |
| 2017/0319634 A1 | 11/2017 | Grant et al. |
| 2017/0326184 A1 | 11/2017 | Patterson et al. |
| 2017/0326202 A1 | 11/2017 | Kelly |
| 2017/0354695 A1 | 12/2017 | Grant et al. |
| 2017/0360856 A1 | 12/2017 | Grant et al. |
| 2017/0368110 A1 | 12/2017 | Grant et al. |

FOREIGN PATENT DOCUMENTS

| | | |
|---|---|---|
| CN | 103156888 A | 6/2013 |
| CN | 103981115 A | 8/2014 |
| CN | 102940652 B | 3/2015 |
| CN | 104546932 A | 4/2015 |
| CN | 104546933 A | 4/2015 |
| CN | 104546934 A | 4/2015 |
| CN | 104546935 A | 4/2015 |
| CN | 104546940 A | 4/2015 |
| CN | 104546942 A | 4/2015 |
| DE | 19826928 A1 | 12/1999 |
| EP | 0778778 A1 | 6/1997 |
| EP | 1448995 A1 | 8/2004 |
| EP | 2687227 A1 | 1/2014 |
| EP | 2810652 A2 | 12/2014 |
| EP | 2832859 A1 | 2/2015 |
| JP | H08259450 A | 10/1996 |
| JP | 2003261453 A | 9/2003 |
| JP | 2005097280 A | 4/2005 |
| JP | 2007084533 A | 4/2007 |
| JP | 2007116991 A | 5/2007 |
| JP | 2009507023 A | 2/2009 |
| JP | 2013527240 A | 6/2013 |
| JP | 2015500792 A | 1/2015 |
| KR | 20100128168 A | 12/2010 |
| WO | WO-9720577 A1 | 6/1997 |
| WO | WO-9855131 A1 | 12/1998 |
| WO | WO-9919459 A1 | 4/1999 |
| WO | WO-0185187 A1 | 11/2001 |
| WO | WO-0207741 A1 | 1/2002 |
| WO | WO-03046580 A1 | 6/2003 |
| WO | WO-2007027761 A2 | 3/2007 |
| WO | WO-2007136719 A2 | 11/2007 |
| WO | WO-2009027753 A1 | 3/2009 |
| WO | WO-2009072889 A1 | 6/2009 |
| WO | WO-2009154463 A2 | 12/2009 |
| WO | WO-2011110918 A1 | 9/2011 |
| WO | WO-2011149335 A1 | 12/2011 |
| WO | WO-2011152566 A2 | 12/2011 |
| WO | WO-2011153226 A2 | 12/2011 |
| WO | WO-2012024638 A2 | 2/2012 |
| WO | WO-2011153226 A3 | 3/2012 |
| WO | WO-2012142605 A1 | 10/2012 |
| WO | WO-2013008039 A2 | 1/2013 |
| WO | WO-2013037068 A1 | 3/2013 |
| WO | WO-2013050792 A1 | 4/2013 |
| WO | WO-2013080561 A1 | 6/2013 |
| WO | WO-2014001368 A1 | 1/2014 |
| WO | WO-2014067976 A1 | 5/2014 |
| WO | WO-2014075745 A1 | 5/2014 |
| WO | WO-2014078911 A1 | 5/2014 |
| WO | WO-2014121298 A2 | 8/2014 |
| WO | WO-2014121304 A1 | 8/2014 |
| WO | WO-2014137211 A1 | 9/2014 |
| WO | WO-2014145958 A2 | 9/2014 |
| WO | WO-2014150094 A1 | 9/2014 |
| WO | WO-2014167338 A1 | 10/2014 |
| WO | WO-2014201037 A2 | 12/2014 |
| WO | WO-2015006355 A2 | 1/2015 |
| WO | WO-2015013214 A2 | 1/2015 |
| WO | WO-2015021936 A1 | 2/2015 |
| WO | WO-2015095241 A2 | 6/2015 |
| WO | WO-2015156419 A1 | 10/2015 |
| WO | WO-2015156519 A1 | 10/2015 |
| WO | WO-2015169944 A1 | 11/2015 |
| WO | WO-2016019506 A1 | 2/2016 |
| WO | WO-2016057671 A1 | 4/2016 |
| WO | WO-2016086161 A1 | 6/2016 |
| WO | WO-2016086206 A1 | 6/2016 |
| WO | WO-2016086209 A1 | 6/2016 |
| WO | WO-2016102950 A1 | 6/2016 |
| WO | WO-2016102951 A1 | 6/2016 |
| WO | WO-2016203218 A1 | 12/2016 |
| WO | WO-2017091753 A1 | 6/2017 |
| WO | WO-2017148596 A1 | 9/2017 |
| WO | WO-2018011594 A1 | 1/2018 |

OTHER PUBLICATIONS

PCT/EP2017/025038 Written Opinion of the International Preliminary Examining Authority dated Jan. 25, 2018.

4D Pharma:"4Dpharma PLC clinical update on blautix (TM), a novel treatment to irritable bowel syndrome," 4DPharma, Jan. 19, 2016, XP002769874, Retrieved from: https://www.directorstalkinterviews.com/4d-pharma-plc-clinical-update-on-blautix-a-novel-treatment-for-irritable-bowel-syndrome/412689588. [Retrieved on May 5, 2017].

"Amedei, A. et al. Multiple sclerosis: the role of cytokines in pathogenesis and in therapies. Int J Mol Sci. Oct. 19, 2012;13(10):13438-60. doi: 10.3390/ijms131013438."

Arenberg, et al., Interferon-y-inducible Protein 10 (IP-10) Is an Angiostatic Factor That Inhibits Human Non-small Cell Lung Cancer (NSCLC) Tumorigenesis and Spontaneous Metastases. 1996. J. Exp.Med. 184:981-92.

Atarashi et al., Th17 Cell Induction by Adhesion of Microbes to Intestinal Epithelial Cells. CELL, vol. 163, No. 2, Oct. 8, 2015. pp. 367-380.

Atarashi, K. et al., Treg induction by a rationally selected mixture of Clostridia strains from the human microbiota. Nature. 2013; 500(7461):232-236.

Atlas, R. Handbook of Microbiological Media, Fourth Edition. CRC Press. 2010.

Ausubel, et al. Current Protocols in Molecular Biology. 1987. Supplement 30.

Ausubel et al., Short protocols in molecular biology. Fifth edition, 2002.

Azad, M.B. et al., Probiotic supplementation during pregnancy or infancy for the prevention of asthma and wheeze: systematic review and meta-analysis BMJ 2013; 347 :f6471.

Bagge, et al., Diversity of spore-forming bacteria in cattle manure, slaughterhouse waste and samples from biogas plants. Journal of applied microbiology. 2010;109: 1549-1565.

Balato, et al., Effects of adalimumab therapy in adult subjects with moderate-to-severe psoriasis on Th17 pathway. (2014) J Eur Acad Dermatol Venereol. 28(8):1016-24.

Banfield, J. & Murphy, K.R., Non-Th2, Late-onset, non-allergic asthma. Copd & Asthma for NPs, A peer-reviewed newsletter, Aug. 2016; 14: 8 Pages.

Berger, S. Gideon guide to medically important bacteria. Gideon E-book Series. 2017 edition. 4 pages.

Bernalier et al. *Ruminococcus hydrogenotrophicus* sp. nov., a new H2/CO2-utilizing acetogenic bacterium isolated from human feces. 1996 Arch. Microbiol. 166 (3), 176-183.

Bertram, J. et al. Establishment of a cloned line of Lewis lung carcinoma cells adapted to cell culture. (1980) Cancer let. 11:63-73.

Birdi, K.S. Handbook of Surface and Colloid Chemistry, 2nd Edition. CRC Press. 1997.

Bottacini, et al., Comparative genomics of the Bifidobacterium brevetaxon. BMC Genomics, 2014; 15:170. DOI:10.1186/1471-1471-2164-15-170.

Brand et al., Collagen-induced arthritis, 2007; Protocol 2(5):1269-1275.

Busing, K. et al., Effects of oral Enterococcus faecium strain DSM 10663 NCIMB 10415 on diarrhoea patterns and performance of sucking piglets. Benef Microbes. Mar. 2015;6(1):41-4. doi: 10.3920/BM2014.0008.

(56) References Cited

OTHER PUBLICATIONS

"Campeau, J.L. et al., Intestinal Epithelial Cells Modulate Antigen-Presenting Cell Responses to Bacterial DNA. Infectionand Immunity. Aug. 2012; 80(8): 2632-2644."
Caspi, P.R. Experimental autoimmune uveoretinitis in the rat and mouse. Curr Protoc Immunol. May 2003;Chapter 15:Unit 15.6. doi: 10.1002/0471142735.im1506s53.
Cekanaviciute, et al., Gut bacteria from multiple sclerosis patients modulate human T cells and exacerbate symptoms in mouse models. PNAS. Jun. 30, 2017; 1-6.
Charriot, et al., Future treatment for ashtma, Eur Respir Rev 2016; 25: 77-92.
Cheluvappa, R. et al., T helper type 17 pathway suppression by appendicitis and appendectomy protects against colitis. Clin Exp Immunol. Feb. 2014;175(2):316-22. doi: 10.1111/cei.12237.
Chen, S. et al., Live combined bacillus subtilis and enterococcus faecium ameliorate murine experimental colitis by immunosuppression. International journal of inflammation. 2014(878054). 7 Pages.
Chi, W. et al., IL-23 promotes CD4+ T cells to produce IL-17 in Vogt-Koyanagi-Harada disease. J Allergy Clin Immunol. May 2007;119(5):1218-24. Epub Mar. 1, 2007.
Chi, W. et al. Upregulated IL-23 and IL-17 in Behçet patients with active uveitis. Invest Ophthalmol Vis Sci. Jul. 2008;49(7):3058-64. doi: 10.1167/iovs.07-1390.
Chiu, et al., Monocolonization of germ-free mice with bacteroides fragilis protects against dectran sulfate sodium-induced acute colitis. Biomed Research International 2014. vol. 2014. Article ID 675786. 9 Pages.
Claesson, et al. Gut microbiota composition correlates with diet and health in the elderly. 2012. Nature, 488, 178-184.
Collins, M.D., et al., *Enterococcus avium* nom. rev., comb. nov.; *E. casseliflavus* nom. rev., comb. nov.; *E. durans* nom. rev., comb. nov.; *E. gallinarum* comb. nov.; and *E. malodoratus* sp. nov. (1984) Int J Syst Evol Microbiol. 34: 220-223.
Colowick, S. and Kaplan, N., Methods of Enzymology. Academic Press, Inc.
Constantinescu et al. Experimental autoimmune encephalomyelitis (EAE) as a model for multiple sclerosis (MS). 2011. Br J Pharmacol. 164(4):1079-1106.
Co-pending U.S. Appl. No. 15/704,245, filed Sep. 14, 2017.
Co-pending U.S. Appl. No. 15/803,721, filed Nov. 3, 2017.
Co-pending U.S. Appl. No. 15/803,723, filed Nov. 3, 2017.
Co-pending U.S. Appl. No. 15/842,635, filed Dec. 14, 2017.
Co-pending U.S. Appl. No. 15/915,889, filed Mar. 8, 2018.
Co-pending U.S. Appl. No. 15/916,167, filed Mar. 8, 2018.
Co-pending U.S. Appl. No. 15/916,202, filed Mar. 8, 2018.
Co-pending U.S. Appl. No. 15/916,205, filed Mar. 8, 2018.
Dahya V. et al., Clostridium ramosum Osteomyelitis in an immunocompetent patient after traumatic injury, Infectious Diseases in Clinical Practice Mar. 12, 2015 Lippincott Williams and Wilkins USA, vol. 23, No. 2, Mar. 12, 2015, pp. 102-104, XP009193312, ISSN: 1056-9103 the whole document.
Darfeuille-Michaud et al. High prevalence of adherent-invasive *Escherichia coli* associated with ileal mucosa in Crohn's disease. .2004. Gastroenterology 127(2):412-21.
Darlington, G.J., Liver Cell Lines. (1987) Meth Enzymol. 151:19-38.
Day, J.G. et al., Cryopreservation and Freeze-Drying Protocols. Springer. 2007. 2nd edition.
Demarche, et al., Detailed analysis of sputum and systemic inflammation in asthma phenotypes: are paucigranulocytic asthmatics really non-inflammatory?, BMC Pulmonary Medicine, 2016; (16)46: 1-13.
Distrutti, et al., Gut Microbiota role in irritable bowel syndrome: New therapeutic strategies. World Journal of Gastroenterology. Feb. 21, 2016; 22(7): p. 2219-2241, XP002769875.
Divyashri et al. Probiotic attributes, antioxidant, anti-inflammatory and neuromodulatory effects of Enterococcus faecium CFR 3003: in vitro and in vivo evidence. (2015) J Med Microbiol. doi: 10.1099/jmm.0.000184.

Duncan et al. (2002) "*Roseburia intestinal* is sp. nov., a novel saccharolytic, butyrate-producing bacterium from human faeces," International Journal System Evolutionary Microbiology. 52:1615-1620.
Duncan et al. (2006) "Proposal of *Roseburia faecis* sp. nov., *Roseburia hominis* sp. nov. and *Roseburia inulinivorans* sp. nov., based on isolates from human faeces," International Journal of Systematic and Evolutionary Microbiology. vol. 56, No. Pt 10, pp. 2437-2441.
Eckburg, PB. et al., Diversity of the human intestinal microbial flora.Science. Jun. 10, 2005;308(5728):1635-8. Epub Apr. 14, 2005.
Fabro, A. et al., The Th17 pathway in the peripheral lung microenvironment interacts with expression of collagen V in the late state of experimental pulmonary fibrosis. (2015) Immunobiology. 220(1):124-35.
Faghih, Z. et a., IL-17 and IL-4 Producing CD8+ T Cells in Tumor Draining Lymph Nodes of Breast Cancer Patients: Positive Association with Tumor Progression. (2013). Iranian Journal of Immunology. 10(4):193-204.
Fahy, J.V. Eosinophilic and neutrophilic inflammation in asthma: insights from clinical studies. Proc Am Thorac Soc. May 1, 2009;6(3):256-9. doi: 10.1513/pats.200808-087RM.
Faith et al. The long-term stability of the human gut microbiota. 2013. Science, 341(6141): 1237439.
Farooq, P.D. et al., Pseudomembranous colitis, Disease-A-Month 2015 Mosby Inc. USA, vol. 61, No. 5, May 1, 2015, pp. 181-206, XP009193313, ISSN: 0011-5029 p. 195.
FDA Orphan Drug Designations. Total Orphan Drugs website. Aug. 2014. Available at http://www.orphan-drugs.org/2014/09/01/fda-orphandrug-designations-august-2014. Accessed on Apr. 13, 2016.
Fenner, et al., *Bacteroides massiliensis* sp. nov., isolated from blood culture of a newborn. International Journal of systematic and evolutionary microbiology, 2005. 55: 1335-1337.
Frank, D. et al., Molecular-phylogenetic characterization of microbial community imbalances in human inflammatory bowel diseases. 2007. PNAS. 104(34):13780-5.
GB Exam and search report dated Aug. 30, 2016 for GB Application No. 1520638.6.
GB Search and Exam report dated Mar. 31, 2016 for GB application 1510469.8.
GB Search and Exam report dated Mar. 31, 2016 for GB application 1510470.6.
GB Search and Exam report dated Apr. 15, 2016 for GB application 1510467.2.
GB Search and Exam report dated Apr. 20, 2016 for GB application 1510466.4.
GB Search and Exam report dated Apr. 20, 2016 for GB application 1510468.0.
GB Search and Exam report dated Aug. 30, 2016 for GB application No. 1520631.1.
GB Search and Exam report dated Nov. 17, 2016 for GB application 1520502.4.
GB Search and Exam report dated Sep. 13, 2016 for GB application 1520497.7.
Gennaro, A.R. "Quality Assurance and Control," from Remington: The Science and Practice of Pharmacy, 2000, Lippincott Williams & Wilkins, 20th ed., pp. 980-983.
Gennaro, A.R., Remington's Pharmaceutical sciences, Mack publishin co. 1985.
Ghadimi, D. et al., Epigenetic imprinting by commensal probiotics inhibits the IL-23/IL-17 axis in an in vitro model of the intestinal mucosal immune system. JLB. 2012;92(4):895-911.
Goldin, B.R. et al., Clinical indications for probiotics: an overview. Clin Infect Dis. Feb. 1, 2008;46 Suppl 2:S96-100; discussion S144-51. doi: 10.1086/523333.
Guide for the care and use of laboratory animals: 8th edition. The national academic press; 2011.
Haabeth et al. A model for cancer-suppressive inflammation. (2012) OncoImmunology 1(1):1146-1152.
Hammerich, L. et al., Interleukins in chronic liver disease: lessons learned from experimental mouse models. (2014) Clin Exp Gastroenterol. 7:297-306.

(56) References Cited

OTHER PUBLICATIONS

Handbook of Experimental Immunology, vols. I IV (D.M. Weir and C.C. Blackwell, eds, 1986, Blackwell Scientific Publications).
International search report with written opinion dated Feb. 26, 2018 for PCT/GB2017/053722.
Hansen, et al., The role of mucosal immunity and host genetics in defining intestinal commensal bacteria. 2010. Curr. Opin. Gastroenterol., 26(6): 564-571.
Holdeman, et al., Eubacterium contortum (Prevot) comb. nov.: Emendation of description and designation of the type strain. International journal of systematic bacteriology. Oct. 1971;21(4): 304-306.
Hougee, et al., Oral treatment with probiotics reduces allergic symptoms in ovalbumin-sensitized mice:a bacterial strain comparative study. Int Arch Allergy Immunol. 2010; 151:107-117.
International Search Report dated Jan. 27, 2017 for International Application No. PCT/GB2016/053622.
International Search Report dated Feb. 17, 2017 for International Application No. PCT/GB2016/053676.
International Search Report dated Aug. 26, 2016 for International application No. PCT/GB2016/051774.
International Search Report dated Aug. 26, 2016 for International application No. PCT/GB2016/051776.
International Search Report dated Sep. 6, 2016 for International application No. PCT/GB2016/051768.
International Search Report dated Sep. 6, 2016 for International application No. PCT/GB2016/051773.
International Search Report dated Sep. 6, 2016for International application No. PCT/GB2016/051770.
International Search Report dated Feb. 2, 2017 for International application No. PCT/GB2016/053620.
International Search Report dated Mar. 6, 2017 for International Application No. PCT/GB2016/053677.
International search report with written opinion dated Jun. 8, 2017 for GB Application No. 1616016.
International search report with written opinion dated Sep. 29, 2017 for GB Application No. 1621123.
International search report with written opinion dated Oct. 16, 2017 for PCT/GB2017/052076.
Ispirli, H. et al., Characterization of functional properties of Enterococcus faecium strains isolated from human gut.Can. J. Microbiol. 61: 861-870 (2015) dx.doi.org/10.1139/cjm-2015-0446.
Jawad, S. et al., Elevated serum levels of interleukin-17A in uveitis patients. Ocul Immunol Inflamm. Dec. 2013;21(6):434-9. doi: 10.3109/09273948.2013.815786. Epub Aug. 19, 2013.
Jiao et al., Blockade of Notch Signaling Ameliorates Murine Collagen-Induced Arthritis via Suppressing Th1 and Th17 Cell Responses. 2014; Pathology, 184(4):1085-1093.
Kailasapathy, K. Microencapsulation of Probiotic Bacteria:Technology and Potential Applications. Curr. Issues Intest. Microbiol. (2002) 3: 39-48.
Kanauchi, et al., Eubacterium limosum ameliorates experimental colitis and metabolite of microbe attenuates colonic inflammatory action with increase of mucosal integrity introduction, China World J Gastroenterol February, Jan. 1, 2006. pp. 1071-1077.
Kanauchi, et al., Eubacterium limosum (probiotic) and its metabolites showed anti-inflammatory effects and increased mucosal barrier function in colitis. S1912.
Kang, S. et al., Dysbiosis of fecal microbiota in Crohn's disease patients as revealed by a custom phylogenetic microarray.Inflamm Bowel Dis. Dec. 2010;16(12):2034-42. doi: 10.1002/ibd.21319.
Karaffova, et al., Interaction of TGF-B4 and IL-17 with IgA secretion in the intestine of chickens fed with E. faecium AL41 and challenged with S. Enteritidis. Research in Veterinary science. 2015:75-79.
Karin, M. Nuclear factor-kappaB in cancer development and progression. Nature. May 25, 2006;441(7092):431-6.
Kitahara, M. et al., Bacteroides plebeius sp. nov. and Bacteroides coprocola sp. nov., isolated from human faeces. International journal of systematic and evolutionary microbiology. 2005; 55: 2143-2147.
Koenders, M.I. et al., Interleukin-17 Acts Independently of TNF-a under Arthritic Conditions. (2006) J. Immunol. 176:6262-6269.
Kverka, M. et al., Oral administration of Parabacteroides distasonis antigens attenuates experimental murine colitis through modulation of immunity and microbiota composition. Clinical & Experimental Immunology. 2010; 163:250-259.
Laukova, A. et al. Benefits of Combinative Application of Probiotic, Enterocin M-Producing Strain Enterococcus Faecium AL41 and Eleutherococcus Senticosus in Rabbits. Folia Microbiol (Praha) 61 (2), 169-177. Sep. 9, 2015.
Lee, et al. Intestinal microbiota in pathophysiology and management of irritable bowel syndrome . 2014. World J Gastroenterol. 20(27): 8886-8897.
Lejeune, FJ. et al., Efficiency of Recombinant Human TNF in Human Cancer Therapy. (2006) Cancer Immun. 6:6.
Leslie, et al., Trehalose and sucrose protect both membranes and proteins in intact bacteria during drying. (1995) Appl. Environ. Microbiol. 61, 3592-3597.
Liu et al. Reclassification of Clostridium coccoides, Ruminococcus hansenii, Ruminococcus hydrogenotrophicus, Ruminococcus luti, Ruminococcus productus and Ruminococcus schinkii as Blautia coccoides gen. nov., comb. nov., Blautia hansenii comb. nov., Blautia hydrogenotrophica comb. nov., Blautia luti comb. nov., Blautia producta comb. nov., Blautia schinkii comb. nov. and description of Blautia wexlerae sp. nov., isolated from human faeces. 2008. Int J Syst Evol Microbiol 58, 1896-1902.
Lodemann, U. et al., Effects of the Probiotic enterococcus faecium and pathogenic escherichia coli strains in a pig and human epithelial intestinal cell model. Hindawi publishing corporation scientifica. 2015(235184) 10 pages.
Lopetuso et al. Commensal Clostridia: leading players in the maintenance of gut homeostasis. 2013. Gut Pathogens, 5: 23.
Lozupone. Diversity, stability and resilience of the human gut microbiota. 2012. Nature. Sep. 13, 2012; 489 (7415): 220-230.
Luger, D. and Caspi, R.R., New perspectives on effector mechanisms in uveitis. (2008) Semin. Immunopathol. 30(2): 134-143.
Lyons, et al., Bacterial strain-specific induction of Foxp3 T regulatory cells is protective in murine allergy models. Clinical & Experimental Allergy. 2010; 40:811-819.
Machiels, K. A decrease of the butyrate-producing species Roseburia hominis and Faecalibacterium prausnitzii defines dysbiosis in patients with ulcerative colitis.Gut. Aug. 2014;63(8):1275-83. doi: 10.1136/gutjnl-2013-304833. Epub Sep. 10, 2013.
MacPherson, AJ. et al., IgA responses in the intestinal mucosa against pathogenic and non-pathogenic microorganisms. Oct. 2001. 3(12). 1021-1035.
MacPherson, AJ., et al., The functions of mucosal T cells in containing the indigenous commensal flora of the intestine.Cell Mol Life Sci. Dec. 2002;59(12):2088-96.
MacSharry et al., Immunomodulatory effects of feeding with bifidobacterium longum on allergen-induced lung inflammation in the mouse. Pulmonary pharmacology & Therapeutics. 2012; 25:325-334.
Maintaining Cultures for Biotechnology and Industry (1996) Jennie C. Hunter-Cevera, Academic Press.
Manni et al., A tale of two cytokines: IL-17 and IL-22 in asthma and infection. Expert Rev Respir Med. Feb. 2014; 8(1): 25-42. doi:10.1586/17476348.2014.854167.
Mansour et al. Isolation of Enterococcus faecium NM113, Enterococcus faecium NM213 and Lactobacillus casei NM512 as novel probiotics with immunomodulatory properties. (2014) Microbiol Immunol. 58(10):559-69.
Masco, L., et al., Identification of Bifidobacterium Species Using rep-PCR Fingerprinting. Systematic and Applied Microbiology 26(4):557-63 • Dec. 2003.
Maya, J.R. et al., Emerging Therapies for Noninfectious Uveitis: What May Be Coming to the Clinics. (2014) J. Ophthalmology. 310329.

(56) References Cited

OTHER PUBLICATIONS

Mazmanian, SK., An immunomodulatory molecule of symbiotic bacteria directs maturation of the host immune system.Cell. Jul. 15, 2005;122(1):107-18.
Meyza, et al. The BTBR mouse model of idiopathic autism—Current view on mechanisms. 2017. Neurosci Biobehav Rev.;76(Pt A):99-110.
Miossec, P. et al. Targeting IL-17 and TH17 cells in chronic inflammation. Nat Rev Drug Discov. Oct. 2012;11(10):763-76. doi: 10.1038/nrd3794.
Mitropoulou, G. et al. Immobilization Technologies in Probiotic Food Production. (2013) Journal Nutr Metab. (2013) 716861.
Miyake, T. et al., Phylogenetic Analysis of the Genus Bifidobacterium and Related Genera Based on 16S rDNA Sequences. Microbiol. Immunol. 1998; 42(10):661-667.
Miyamoto-Shinohara et al. Survival of freeze-dried bacteria. J Gen Appl Microbiol 54(1):9-24 (2008).
Miyauchi, E., Control of multiple sclerosis by gut microbiota. Journal of clinical and experimental medicine. 2015. vol. 253 No. 5.2, pp. 445-450.
Molecular Biology Techniques: An Intensive Laboratory Course, (Ream et al., eds., 1998, Academic Press).
Monteleone, I. et al., Th17-related cytokines: new players in the control of chronic intestinal inflammation. (2011) BMC Medicine. 2011, 9:122.
Mucientes, A. et al., Specific association of IL17A genetic variants with panuveitis. (2015) Br J Ophthalmol. 99(4):566-70.
Mukai et al., SH3BP2 Gain-Of-Function Mutation Exacerbates Inflammation and Bone Loss in a Murine Collagen-Induced Arthritis Model, 2014 PLoS One 9(8): e105518.
Narushima, et al., Characterization of the 17 strains of regulatory T cell-inducing human-derived Clostridia. Gut Microbes Mar. 18, 2014; 5:3, 333-339.
Notice of allowance dated Sep. 1, 2017 for U.S. Appl No. 15/357,850.
Notice of Allowance dated Nov. 22, 2017 for U.S. Appl. No. 15/359,988.
Numasaki, M. et al., IL-17 Enhances the Net Angiogenic Activity and In Vivo Growth of Human Non-Small Cell Lung Cancer in SCID Mice through Promoting CXCR-2-Dependent Angiogenesis. (2005) J. Immunol. 175: 6177-6189.
Numasaki, M. et al., Interleukin-17 promotes angiogenesis and tumor growth. Blood. Apr. 1, 2003;101(7):2620-7. Epub Oct. 31, 2002.
Office Action dated Jan. 2, 2018 for U.S. Appl. No. 15/357,936.
Office Action dated Jan. 11, 2005 for U.S. Appl. No. 10/285,224.
Office Action dated Jan. 26, 2009 for U.S. Appl. No. 10/275,706.
Office Action dated Feb. 18, 2010 for U.S. Appl. No. 10/285,224.
Office Action dated Mar. 13, 2013 for U.S. Appl. No. 12/760,926.
Office Action dated Mar. 26, 2007 for U.S. Appl. No. 10/275,706.
Office Action dated Apr. 4, 2008 for U.S. Appl. No. 10/285,224.
Office Action dated May 2, 2007 for U.S. Appl. No. 10/285,224.
Office Action dated May 2, 2008 for U.S. Appl. No. 10/275,706.
Office Action dated May 25, 2016 for U.S. Appl. No. 14/249,710.
Office Action dated May 26, 2009 for U.S. Appl. No. 10/285,224.
Office Action dated May 26, 2017 for U.S. Appl. No. 15/357,850.
Office Action dated May 30, 2006 for U.S. Appl. No. 10/285,224.
Office Action dated Jun. 26, 2017 for U.S. Appl. No. 15/357,936.
Office Action dated Jul. 6, 2017 for U.S. Appl. No. 15/070,605.
Office action dated Jul. 8, 2015 for U.S. Appl. No. 14/349,907.
Office Action dated Jul. 31, 2017 for U.S. Appl. No. 15/359,988.
Office Action dated Aug. 10, 2017 for U.S. Appl. No. 15/357,850.
Office Action dated Aug. 21, 2013 for U.S. Appl. No. 12/760,926.
Office Action dated Sep. 4, 2015 for U.S. Appl. No. 14/249,710.
Office Action dated Sep. 17, 2010 for U.S. Appl. No. 10/285,224.
Office Action dated Oct. 12, 2005 for U.S. Appl. No. 10/285,224.
Office Action dated Oct. 28, 2009 for U.S. Appl. No. 10/275,706.
Office Action dated Oct. 30, 2008 for U.S. Appl. No. 10/285,224.
Office Action dated Nov. 2, 2017 for U.S. Appl. No. 15/700,007.
Office Action dated Nov. 6, 2006 for U.S. Appl. No. 10/285,224.
Office Action dated Nov. 23, 2015 for U.S. Appl. No. 14/232,475.
Office Action dated Nov. 24, 2017 for U.S. Appl. No. 15/359,972.
Office Action dated Nov. 24, 2017 for U.S. Appl. No. 15/679,857.
Office Action dated Dec. 6, 2017 for U.S. Appl. No. 15/592,178.
Office Action dated Dec. 13, 2012 for U.S. Appl. No. 12/760,926.
Office Action dated Dec. 19, 2005 for U.S. Appl. No. 10/275,706.
Oladipo, et al., Bioprotective potential of bacteriocinogenic enterococcus gallinarum strains isolated from some Nigerian fermented foods, and of their bacteriocins. Polish Journal of Microbiology. 2014; 63(4): 415-422.
Overstreet et al. 'Dysbiosis Characterized by Reduced Abundance of Roseburia is Associated With Increased Severity of Colitis in IL-10–/– Mice'. Gastroenterology. 2011, vol. 140, No. 5, Suppl. 1, pp. S-696.
Pace et al. Macrophage activiation: Priming activity from a T-cell hybridoma is attributable to interferon. (1983) PNAS. 80:3782-6.
Parabacteroides distasonis (Eggerth and Gagnon) Sakamoto and Benno (ATCC 8503). Sep. 19, 2017. 2 Pages.
Park, S.K. et al., *Blautia stercoris* sp. nov., isolated from human faeces. International journal of systematic and evolutionary microbiology. 2012; 62(4): 776-779.
Patel., R. et al., Determination of 16S rRNA sequences of enterococci and application to species identification of nonmotile *Enterococcus gallinarum* isolates. Journal of clinical microbiology, 1998; 36(11):3399-3407.
PCR (Introduction to Biotechniques Series), 2nd ed. (Newton & Graham eds., 1997, Springer Verlag).
PCT/EP2017/025038 Written Opinion of the International Preliminary Examining Authority dated Jan. 1, 2018.
Pearson, WR. An introduction to sequence similarity ("Homology") searching. Current protocols in bioinformatics/editoral board, Andreas D Baxevanis. 2013; 0 3:10. 1002/0471250953.bi0301s42. doi:10.1002/0471250953.bi0301s42.
Petersen et al. Intestinal colonization with phylogenetic group B2 *Escherichia coli* related to inflammatory bowel disease: a systematic review and meta-analysis. 2015. Scand J Gastroenterol. ;50(10):1199-207.
Rajilic-Stojanovic, et al. The first 1000 cultures species of the human gastrointestinal micriobiota. FEMS Mlcriobiol Rev, vol. 38, 2014. pp. 996-1047.
Remington. Remington: The science and practice of pharmacy. 20th Edition. Gennaro, Eds. Lippincott Williams & Wilkins, 2003.
Riquelme. Will 4D Pharma be UK's next Microbiome leader? Feb. 2, 2015, LABIOTECH.eu [online].
Robinson, et al. Inside information—The unique features of visceral sensation. 2008. Mol Interv, 8(5):242-253.
Rockwell, S.C. et al., Characteristics of a Serially Transplanted Mouse Mammary Tumor and Its Tissue-Culture-Adapted Derivative. (1972) J Natl Cancer Inst. 49:735-49.
Sagar, et al., Bifidobacterium breve and lactobacillus rhamnosus treatment is as effective as budesonide at reducing inflammation in a murine model for chronic asthma. Respiratory Research. 2014; 15(46):1-17.
Sakamoto, M. et al., Reclassification of Bacteroides distasonis, Bacteroides goldsteinii and Bacteroides merdae as Parabacteroides distasonis gen. nov., comb. nov., Parabacteroides goldsteinii comb. nov. and Parabacteroides merdae comb. nov. International journal of systematic and evolutionary microbiology. 2006; 56: 1599-1605.
Salix Pharmaceuticals, Inc. FDA Highlights of Prescribing Information—XIFAXAN (rifaximin tablet). Revised Nov. 2015.
Sambrook, J.F. et al., Molecular Cloning: A Laboratory Manual, 3rd ed. Cold spring harbor laboratory press. 2001.
Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.
Scher et al., Expansion of intestinal Prevotella copri correlates with enhanced susceptibility to arthritis. 2013; eLIFE 2, e01202, 20 Pages.
Schieck, M. et al., Genetic variation in TH17 pathway genes, childhood asthma, and total serum IgE levels.(2014) J Allergy Clin Immunol. 133(3):888-91.

(56) References Cited

OTHER PUBLICATIONS

Schleifer, K.H. et al., Transfer of *Streptococcus faecalis* and *Streptococcus faecium* to the Genus *Enterococcus* nom. rev. as *Enterococcus faecalis* comb. nov. and *Enterococcus faecium* comb. nov. Int J Syst Evol Microbiol, Jan. 1984 34: 31-34, doi:10.1099/00207713-34-1-31.
Schmitz, S. et al., A prospective, randomized, blinded, placebo-controlled pilot study on the effect of Enterococcus faecium on clinical activity and intestinal gene expression in canine food-responsive chronic enteropathy. J Vet Intern Med. Mar.-Apr. 2015;29(2):533-43. doi: 10.1111/jvim.12563. Epub Mar. 16, 2015.
Schouten, et al., Cow milk allergy symptoms are reduced in mice fed dietary synbiotics during oral sensitization with whey. Nutritional Immunology. 2015; 139(7):1390-403.
Schwiertz, et al., Quantification of Different *Eubacterium* spp. in Human Fecal Samples with Species-Specific 16S rRNA-Targeted Oligonucleotide Probes. Applied and environmental biology, vol. 66, No. 1, Jan. 1, 2000; pp. 375-382.
Severijnen, et al., Chronic Arthritis Induced in Rats by Cell Wall Fragments of *Eubacterium* Species from the Human Intestinal Flora. Infection and Immunity, Feb. 1990; 58(2): p. 523-528.
Sgadari, C. et al., Interferon-inducible protein-10 identified as a mediator of tumor necrosis in vivo. (1996) PNAS. 93:13791-6.
Sgadari et al. Mig, the Monokine Induced by Interferon-g, Promotes Tumor Necrosis In Vivo. (1997) Blood. 89:2635-43.
Shabgah, A.G. et al., Interleukin-17 in human inflammatory diseases. Postepy Dermatol Alergol. Aug. 2014; 31(4): 256-261.
Simpson-Herren, L. et al., Kinetic parameters and growth curves for experimental tumor systems. Cancer Chemother Rep. Jun. 1970;54(3):143-74.
Sisson, G. et al., Randomised clinical trial: a liquid multi-strain probiotic vs. placebo in the irritable bowel syndrome—a 12 week double-blind study. Aliment Pharmacol Ther. 2014; 40: 51-62.
Sivieri, K. et al., Probiotic enterococcus faecium CRL 183 inhibit chemically induced colon cancer in male wistar rats. Eur Food Res Technol. 2008; 228:231-237.
Smith, T.F. et al., Comparison of biosequences. (1981) Adv. Appl. Math. 2: 482-489.
Song et al., Impact of Schistosoma japonicum Infection on Collagen-Induced Arthritis in DBA/1 Mice: A Murine Model of Human Rheumatoid Arthritis. 2011; PLoS ONE 6, e23453, 10 pAGES.
Spor, A. et al., Unravelling the effects of the environment and host genotype on the gut microbiome. Nat Rev Microbiol. Apr. 2011;9(4):279-90. doi: 10.1038/nrmicro2540.
Srutkova, D. et al., Efficiency of PCR-based methods in discriminating *Bifidobacterium longum* ssp. *longum* and *Bifidobacterium longum* ssp. infantis strains of human origin.J Microbiol Methods. Oct. 2011;87(1):10-6. doi: 10.1016/j.mimet.2011.06.014. Epub Jul. 2, 2011.
Stanton et al. (1983) "*Roseburia cecicola* gen. nov., sp. nov., a Motile, Obligately Anaerobic Bacterium from a Mouse Cecum," Int. J. Syst. Bacterial. 33:618-627.
Stoll et al., Altered microbiota associated with abnormal humoral immune responses to commensal organisms in enthesitis-related arthritis, 2014; Arthritis Res Ther. 16:486.
Strickertsson, J.A. et al., Enterococcus faecalis Infection and Reactive Oxygen Species Down-Regulates the miR-17-92 Cluster in Gastric Adenocarcinoma Cell Culture. Genes 2014, 5(3), 726-738.
Strobel, H.J. Basic laboratory culture methods for anaerobic bacteria. Methods Mol Biol. 2009;581:247-61. doi: 10.1007/978-1-60761-214-8_16.
Strus et al. Distinct effects of Lactobacillus plantarum KL30B and *Escherichia coli* 3A1 on the induction and development of acute and chronic inflammation. 2015. Cent Eur J Immunol.40(4):420-30.
Sun, D. et al., The role of Th17-associated cytokines in the pathogenesis of experimental autoimmune uveitis (EAU). (2015) Cytokine. 74(1):76-80.
Tanaka, K. and Watanabe, K., In Vitro tebipenem activity against anaerobic bacteria. Japanese Journal of Chemotherapy. Mar. 2009. vol. 57 S-1.

Tap et al. Towards the human intestinal microbiota phylogenetic core. 2009. Environ Microbiol, 11(10):2574-84.
Tesmer, LA. et al., Th17 cells in human disease. Immunol Rev. 2008;223:87-113.
Toomer, O. et al., Maternal and postnatal dietary probiotic supplementation enhances splenic regulatory T helper cell population and reduces peanut allergen-induced hypersensitivity responses in mice. Immunobiology. 209; 2014: 661-670.
Tsukinowa, et al., Fecal microbiota of a dugong (Dugong dugong) in captivity at Toba Aquarium. J. Gen. Appl. Microbiol., 54, 25-38 (2008).
Turnbaugh et al. A core gut microbiome in obese and lean twins. Jan. 22, 2009. Nature, 457(7228): 480-484.
Udayappan, et al., Oral treatment with Eubacterium hallii improves insulin sensitivity in db/db mice. NPJ Biofilms and microbiomes, vol. 2, Jul. 6, 2016; p. 16009.
Udayappan et al., PS4-5. Administration of Eubacterium hallii improves insulin sensitivity and degree of liversteatosis in male db/db mice. Nederlands tijdschrift voor diabetologie, vol. 11, No. 4., Nov. 23, 2013.pp. 145.
U.S. Appl. No. 15/631,952 Office Action dated Feb. 16, 2018.
U.S. Appl. No. 15/679,857 Office Action dated Feb. 14, 2018.
U.S. Appl. No. 15/803,723 Notice of Allowance dated Feb. 13, 2018.
Van De Veerdonk, et al., The Anti-CD20 antibody rituximab reduces the Th17 cell response. Arthritis & Rheumatism. Jun. 2011; 63(6):1507-1516.
Vetrovsky, T. and Baldrian, P., The variability of the 16S rRNA gene in bacterial genomes and its consequences for bacterial community analyses. Plos One. Feb. 2013; 8(2): e57923.
Wang et al. 16S rRNA gene-based analysis of fecal microbiota from preterm infants with and without necrotizing enterocolitis. 2009. ISME J. 3(8): 944-954.
Workman et al. Guidelines for the welfare and use of animals in cancer research (2010) Br. J. Cancer. 102:1555-77.
Wunderlich, P.F. et al., Double-blind report on the efficacy of lactic acid-producing enterococcus SF68 in the prevention of antibiotic-associated diarrhoea and in the treatment of acute diarrhoea. The journal of international medical research. 1989; 17: 333-338.
Xie et al. Short communication: Modulation of the small intestinal microbial community composition over short-term or long-term administration with Lactobacillus plantarum ZDY2013. 2016. Journal Dairy Sci. 99:6913-6921.
Xu, et al., The endogenous hydrogen sulfide producing enzyme cystathionine-i synthase contributes to visceral hypersensitivity in a rat model of irritable bowel syndrome. Molecular Pain, Biomed central, London, GB. Aug. 6, 2009; 5(1):p. 44.
Yang, J. et al., Targeting Th17 cells in autoimmune diseases. Trends Pharmacol Sci. Oct. 2014;35(10):493-500. doi: 10.1016/j.tips.2014. 07.006. Epub Aug. 14, 2014.
Ye, X. et al., The Role of IL-23/Th17 Pathway in Patients with Primary Immune Thrombocytopenia. (2015) PLoS One. 10(1):e0117704.
Yin, X. et al., Combined effect of five single nucleotide polymorphisms related to IL23/Th17 pathway in the risk of psoriasis. Immunogenetics. Mar. 2014;66(3):215-8. doi: 10.1007/s00251-013-0756-z. Epub Jan. 14, 2014.
Yq et al. Therapeutic Modulation of the Gut Microbiota in IBD—More Questions to Be Answered. (2016). J. Dig. Dis., Oct. 15, 1751-2980, 12422, Epub ahead of print.
Yutin, N. and Galperin, M.Y., A genomic update on clostridial phylogeny:Gram-negative spore formers and other misplaced clostridia. Environmental microbiology. 20136; 15(10): 2631-2641.
Zhang, B. et al., Oral administration of enterococcus faecalis FK-23 suppresses Th17 cell development and attenuates allergic airway responses in mice. International journal of molecular medicine. 2012; 30:248-254.
Zhang, B. et al., The Prevalence of Th17 Cells in Patients With Gastric Cancer. 2008. Biochem Biophys Res Commun 374 (3), 533-537.

(56) References Cited

OTHER PUBLICATIONS

Zhang, et al., The Activation of NF-κB in Infiltrated Mononuclear Cells Negatively Correlates with Treg Cell Frequency in Oral Lichen Planus. Inflammation. Aug. 2015;38(4):1683-9. doi: 10.1007/s10753-015-0145-x.

Zheng, B. et al., Bifidobacteriu breve attenuates murine dextran sodium sulfate-induced colitis and increases regulatory T cell responses. PLOS one. May 2014; 9(5).

Zhongyuan, T. et al., The inflammation regulation effects of enterococcus faecium HDRsEf1 on human enterocyte-like Ht-29 cells. Animal cells and systems. Mar. 2016;20(2):70-76.

Zhou et al. Central and peripherial hypersensitivity in the irritable bowel syndrome. 2010. Pain. 148(3): 454-461.

Zhu, S. and Qian, Y., IL-17/IL-17 receptor system in autoimmune disease: mechanisms and therapeutic potential. Clinical Science (2012) 122, 487-511.

Zitomersky, N. et al., Characterization of Adherent Bacteroidales from Intestinal Biopsies of Children and Young Adults with Inflammatory Bowel Disease. PLOS one. 2013; 8(6).

Zitvogel, et al., Type I interferons in anticancer immunity. Nature Reviews. Jul. 2015:405-414.

4d Pharma Plc: "Clinical Update—RNS—London Stock Exchange", Jul. 19, 2016.

Anonymous: "4D pharma's Blautix for Irritable Bowel Syndrome shows positive impact—pharmaceutical daily news", Dec. 13, 2016.

Bernalier, A., et al., "Diversity of H2/CO2-utilizing acetogenic Bacteria from Feces of Non-Methane-Producing Humans", Current Microbiology vol. 33 (Aug. 1996), pp. 94-99, Springer-Vertag New York Inc., USA.

Bernalier et al., "Acetogenesis from H02 and C0-2 By Methane and Non-Methane-Producing Human Colonic Bacterial Communities" Fems Microbiology Ecology. vol. 19. No. 3. 1996. pp. 193-202. XP000979130.

Co-pending U.S. Appl. No. 15/906,988, filed Feb. 27, 2018.

DMSZ: Opening of Ampoules and Rehydration of Dried Cultures; (http://web.archive.org/web/20000 52411541 O/www.dsmz.de/open. htm); updated of website on Mar. 2000.

GB1612190.7 International Search Report dated Apr. 12, 2017.

O'Sullivan et al., "Bacterial Supplementation in the Irritable Bowel Syndrome. A Randomised Double-Blind Placebo-Controlled Crossover Study", Digest Liver Dis. 2000. pp. 294-301.

PCT/EP2017/025038 International Search Report and Written Report dated Jun. 12, 2017.

PCT/GB2017/052077 International Search Report dated Oct. 16, 2017.

PCT/GB2017/052077 Written Opinion dated Oct. 16, 2017.

U.S. Appl. No. 15/359,144 Office Action dated Apr. 10, 2018.

U.S. Appl. No. 15/359,972 Office Action dated Apr. 4, 2018.

U.S. Appl. No. 15/673,270 Office Action dated Apr. 10, 2018.

Van Nevel et al., "Conrol of Rumen Methanogenesis." Environmental Monitoring and Assessment. vol. 42, 1996, pp. 73097, XP000979267.

PCT/EP2017/025038 International Preliminary Report on Patentability dated Jun. 6, 2018, 8 Pages.

PCT/GB2017/052076 Written Opinion of the International Preliminary Examining Authority dated Jun. 21, 2018, 11 Pages.

PCT/GB2017/052077 Written Opinion of the International Preliminary Examining Authority dated Jun. 21, 2018, 10 Pages.

* cited by examiner

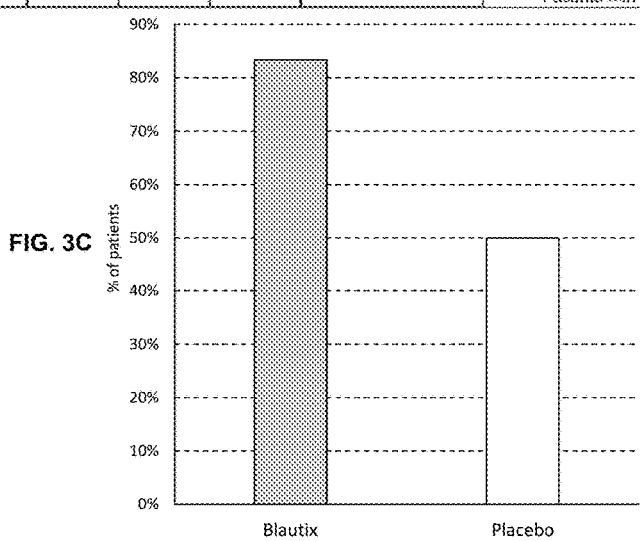

FIG. 4A
VERUM group
| RANDOM NUMBER | DAY 1 CMAX | DAY 15 CMAX | | H2 Corrected | RANDOM NUMBER | DAY 1 CMAX | DAY 15 CMAX |
|---|---|---|---|---|---|---|---|
| 3.02 | 89.8 | 23.0 | | | 3.02 | 123.0 | 34.0 |
| 3.04 | 68.0 | 21.0 | | | 3.04 | 78.0 | 15.0 |
| 3.05 | 138.4 | 112.8 | | | 3.05 | 163.0 | 167.8 |
| 3.07 | 56.8 | 37.6 | | | 3.07 | 71.0 | 46.0 |
| 3.09 | 96.8 | 52.8 | | | 3.09 | 121.0 | 66.0 |
| 3.11 | 63.0 | 104.9 | | | 3.11 | 75.0 | 128.0 |
| 3.12 | 12.3 | 38.7 | | | 3.12 | 16.0 | 53.0 |
| 3.13 | 106.3 | 82.5 | | | 3.13 | 118.0 | 85.0 |
| 3.15 | 115.7 | 53.8 | | | 3.15 | 155.0 | 63.0 |
| 3.17 | 97.8 | 83.7 | | | 3.17 | 134.0 | 139.0 |
| 3.19 | 51.1 | 66.1 | | | 3.19 | 72.0 | 87.0 |
| 3.21 | 144.0 | 71.4 | | | 3.21 | 184.0 | 75.0 |
| 3.22 | 52.7 | 63.9 | | | 3.22 | 59.0 | 55.0 |
| 3.24 | 27.1 | 26.7 | | | 3.24 | 29.0 | 27.0 |
| | | T Test unilateral | 0.02032643 | | | | T Test unilateral | 0.04798585 |
| | Day 1 | Day 15 | | | | Day 1 | Day 15 |
| MEAN | 79.7 | 58.5 | | | MEAN | 96.4 | 75.0 |
| SD | 38.7 | 29.5 | | | SD | 46.5 | 43.0 |
| N | 14 | 14 | | | N | 14 | 14 |
| MEDIAN | 78.9 | 53.3 | | | MEDIAN | 96.5 | 64.5 |
| MIN | 12.3 | 21.0 | | | MIN | 16.0 | 25.0 |
| MAX | 144.0 | 112.8 | | | MAX | 163.0 | 167.8 |
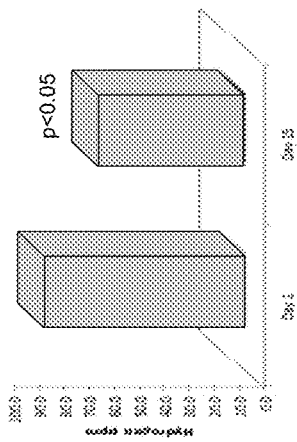
FIG. 4B
Hydrogen uncorrected
p<0.05
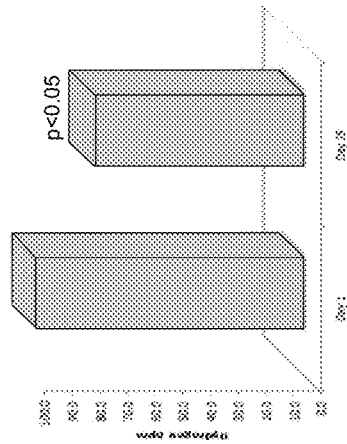
FIG. 4C
Hydrogen corrected
p<0.05

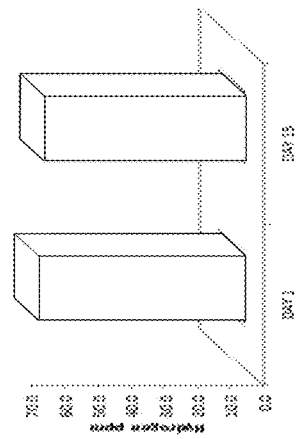
FIG. 5B
Hydrogen uncorrected placebo
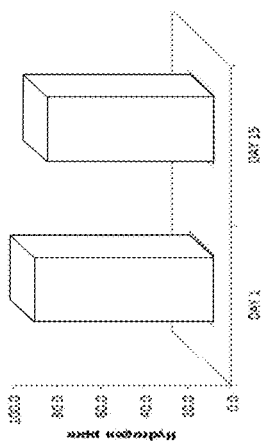
FIG. 5C
Hydrogen corrected placebo
FIG. 5A

|  | DAY 1 | DAY 15 | N |
|---|---|---|---|
| VERUM Group | 79.7 | 58.5 | 14 |
| PLACEBO Group | 61.7 | 60 | 7 |

|  | DAY 1 | DAY 15 | N |
|---|---|---|---|
| VERUM Group | 96.4 | 75 | 14 |
| PLACEBO Group | 82 | 75.9 | 7 |

COMPOSITIONS COMPRISING BACTERIAL STRAINS

SEQUENCE LISTING

The instant application contains a Sequence Listing which has been submitted electronically in ASCII format and is hereby incorporated by reference in its entirety. Said ASCII copy, created on Jul. 4, 2017, is named P068687WO_Sequence_Listing.txt and is 12,288 bytes in size.

TECHNICAL FIELD

This invention is in the field of compositions comprising bacterial strains isolated from the mammalian digestive tract and the use of such compositions in the treatment of disease.

BACKGROUND TO THE INVENTION

The human intestine is thought to be sterile in utero, but it is exposed to a large variety of maternal and environmental microbes immediately after birth. Thereafter, a dynamic period of microbial colonization and succession occurs, which is influenced by factors such as delivery mode, environment, diet and host genotype, all of which impact upon the composition of the gut microbiota, particularly during early life. Subsequently, the microbiota stabilizes and becomes adult-like [1]. The human gut microbiota contains more than 1500 different phylotypes dominated in abundance levels by two major bacterial divisions (phyla), the Bacteroidetes and the Firmicutes [2-3]. The successful symbiotic relationships arising from bacterial colonization of the human gut have yielded a wide variety of metabolic, structural, protective and other beneficial functions. The enhanced metabolic activities of the colonized gut ensure that otherwise indigestible dietary components are degraded with release of by-products providing an important nutrient source for the host and additional health benefits. Similarly, the immunological importance of the gut microbiota is well-recognized and is exemplified in germfree animals which have an impaired immune system that is functionally reconstituted following the introduction of commensal bacteria [4-6].

Dramatic changes in microbiota composition have been documented in gastrointestinal disorders such as inflammatory bowel disease (IBD). For example, the levels of *Clostridium* cluster XIVa and *Clostridium* cluster XI (*F. prausnitzii*) bacteria are reduced in IBD patients whilst numbers of *E. coli* are increased, suggesting a shift in the balance of symbionts and pathobionts within the gut [7-11]. In recognition of the potential positive effect that certain bacterial strains may have on the animal gut, various strains have been proposed for use in the treatment of various diseases (see, for example, [12-15]). A number of strains, including mostly *Lactobacillus* and *Bifidobacterium* strains, have been proposed for use in treating various bowel disorders (see [16] for a review). Strains of the genus *Blautia* have also been proposed for use in modulating the microbial balance of the digestive ecosystem in IBS patients (WO 01/85187). However, the relationship between different bacterial strains and different diseases, and the precise effects of particular bacterial strains on the gut and at a systemic level and on any particular types of diseases, are poorly characterised.

There is a requirement for the potential effects of gut bacteria to be characterised so that new therapies using gut bacteria can be developed.

US 2010/0247489 describes the use of mineral nutrients to treat digestive disorders. US'789 proposes optionally also using numerous different genera of bacteria to prevent a wide variety of abdominal symptoms but does not link any bacteria to any diseases or symptoms.

WO 2016/086206 suggests that bacteria in the order Clostridiales can be used to treat or prevent various conditions but does not link any bacteria to any diseases or symptoms.

WO 2012/142605 proposes that it may be possible to treat a number of different diseases with a combination of microorganisms. WO'605 suggests a large number of possible bacterial species that could be employed, but there is no teaching in WO'605 as to how any of the proposed bacterial species could be used to treat any of the diseases proposed.

WO 02/07741 suggests using various bacteria from the class Clostridia to treat gastrointestinal disorders but does not link any bacteria to any diseases or symptoms. WO 2016/086209 suggests using a large number of possible bacteria in the order Clostridiales to decrease the secretion of pro-inflammatory cytokines and/or increase the secretion of anti-inflammatory cytokines, but there is no teaching as to how any of the proposed bacterial species could be used to treat any of the diseases proposed.

SUMMARY OF THE INVENTION

The inventors have developed new therapies for treating and preventing diarrhea and/or constipation. In particular, the inventors have identified that bacterial strains from the genus *Blautia* can be effective for reducing diarrhea and/or constipation. As described in the examples, oral administration of compositions comprising *Blautia hydrogenotrophica* may reduce diarrhea and/or constipation in patients having irritable bowel syndrome (IBS). Therefore, in a first embodiment, the invention provides a composition comprising a bacterial strain of the genus *Blautia*, for use in a method of treating or preventing diarrhea and/or constipation.

In preferred embodiments, the invention provides a composition comprising a bacterial strain of the genus *Blautia*, for use in a method of treating or preventing diarrhea and/or constipation in a subject diagnosed with Crohn's disease, ulcerative colitis, or, more preferably, IBS. In some embodiments, the subject diagnosed with IBS has IBS with both diarrhea and constipation. In some embodiments, the subject diagnosed with IBS has IBS with diarrhea but without constipation or with only a small amount of constipation. In some embodiments, the subject diagnosed with IBS has IBS with constipation but without diarrhea or with only a small amount of diarrhea.

In preferred embodiments of the invention, the bacterial strain in the composition is of *Blautia hydrogenotrophica*. Closely related strains may also be used, such as bacterial strains that have a 16s rRNA sequence that is at least 95%, 96%, 97%, 98%, 99%, 99.5% or 99.9% identical to the 16s rRNA sequence of a bacterial strain of *Blautia hydrogenotrophica*. Preferably, the bacterial strain has a 16s rRNA sequence that is at least 95%, 96%, 97%, 98%, 99%, 99.5% or 99.9% identical to SEQ ID NO:5. Most preferably, the bacterial strain in the composition is the *Blautia hydrogenotrophica* strain deposited under accession number DSM 10507/14294.

In further embodiments of the invention, the bacterial strain in the composition is of *Blautia stercoris*. Closely related strains may also be used, such as bacterial strains that have a 16s rRNA sequence that is at least 95%, 96%, 97%, 98%, 99%, 99.5% or 99.9% identical to the 16s rRNA sequence of a bacterial strain of *Blautia stercoris*. Preferably, the bacterial strain has a 16s rRNA sequence that is at least 95%, 96%, 97%, 98%, 99%, 99.5% or 99.9% identical to SEQ ID NO:1 or 3. Preferably, the sequence identity is to SEQ ID NO:3. Preferably, the bacterial strain for use in the invention has the 16s rRNA sequence represented by SEQ ID NO:3.

In further embodiments of the invention, the bacterial strain in the composition is of *Blautia wexlerae*. Closely related strains may also be used, such as bacterial strains that have a 16s rRNA sequence that is at least 95%, 96%, 97%, 98%, 99%, 99.5% or 99.9% identical to the 16s rRNA sequence of a bacterial strain of *Blautia wexlerae*. Preferably, the bacterial strain has a 16s rRNA sequence that is at least 95%, 96%, 97%, 98%, 99%, 99.5% or 99.9% identical to SEQ ID NO:2 or 4. Preferably, the sequence identity is to SEQ ID NO:4. Preferably, the bacterial strain for use in the invention has the 16s rRNA sequence represented by SEQ ID NO:4.

In certain embodiments, the composition of the invention is for oral administration. Oral administration of the strains of the invention can be effective for treating diarrhea and/or constipation. Also, oral administration is convenient for patients and practitioners and allows delivery to and/or partial or total colonisation of the intestine.

In certain embodiments, the composition of the invention comprises one or more pharmaceutically acceptable excipients or carriers.

In certain embodiments, the composition of the invention comprises a bacterial strain that has been lyophilised. Lyophilisation is an effective and convenient technique for preparing stable compositions that allow delivery of bacteria, and is shown to provide effective compositions in the examples.

In certain embodiments, the invention provides a food product comprising the composition as described above.

In certain embodiments, the invention provides a vaccine composition comprising the composition as described above.

Additionally, the invention provides a method of treating or preventing diarrhea and/or constipation, comprising administering a composition comprising a bacterial strain of the genus *Blautia*.

In preferred embodiments, the invention provides a composition comprising a bacterial strain of the genus *Blautia*, for use in a method of treating or preventing a disease associated with Enterobacteriaceae infection, such as *E. coli* infection. In certain embodiments, the compositions of the invention are for use in treating or preventing diarrhea, gastroenteritis, urinary tract infection or neonatal meningitis.

In further preferred embodiments, the compositions of the invention are for use in reducing the level of Enterobacteriaceae in the gastrointestinal tract, preferably the level of *E. coli*, in the treatment or prevention of IBS, Crohn's disease, ulcerative colitis, functional dyspepsia, diarrhea, gastroenteritis, urinary tract infection or neonatal meningitis.

In particularly preferred embodiments, the compositions of the invention are for use a method of treating or preventing diarrhea associated with Enterobacteriaceae infection, such as *E. coli* infection, or are for use in reducing the level of Enterobacteriaceae in the gastrointestinal tract, preferably the level of *E. coli*, in the treatment or prevention of diarrhea.

BRIEF DESCRIPTION OF DRAWINGS

FIG. 3a: Hydrogen breath test Cmax results for day 1, day 2, day 15 and day 16 for IBS patients treated with Blautix (FIG. 3a). FIG. 3b: Hydrogen breath test Cmax results for day 1, day 2, day 15 and day 16 for and IBS patients treated with placebo (FIG. 3b). FIG. 3c is a graph comparing the percentage of Blautix treated patients with a reduction in hydrogen between the mean of days 15 and 16 and the mean of days 1 and 2 to the percentage of placebo treated patients with a reduction in hydrogen between these time points.

FIG. 4a: Hydrogen uncorrected and hydrogen corrected breath test paired data for day 1 and day 15 for Blautix treated IBS patients; FIG. 4b: graph comparing mean hydrogen uncorrected breath test results for day 1 and day 15 for the Blautix treatment group; FIG. 4c: graph comparing mean hydrogen corrected breath test results for day 1 and day 15 for the Blautix treatment group.

FIG. 5a: Hydrogen uncorrected and hydrogen corrected breath test paired data for day 1 and day 15 for placebo treated IBS patients; FIG. 5b: graph comparing mean hydrogen uncorrected breath test results for day 1 and day 15 for the placebo group; FIG. 5c: graph comparing mean hydrogen corrected breath test results for day 1 and day 15 for the placebo group.

FIG. 6b: corrected hydrogen).

DISCLOSURE OF THE INVENTION

Bacterial Strains

Figure 2:
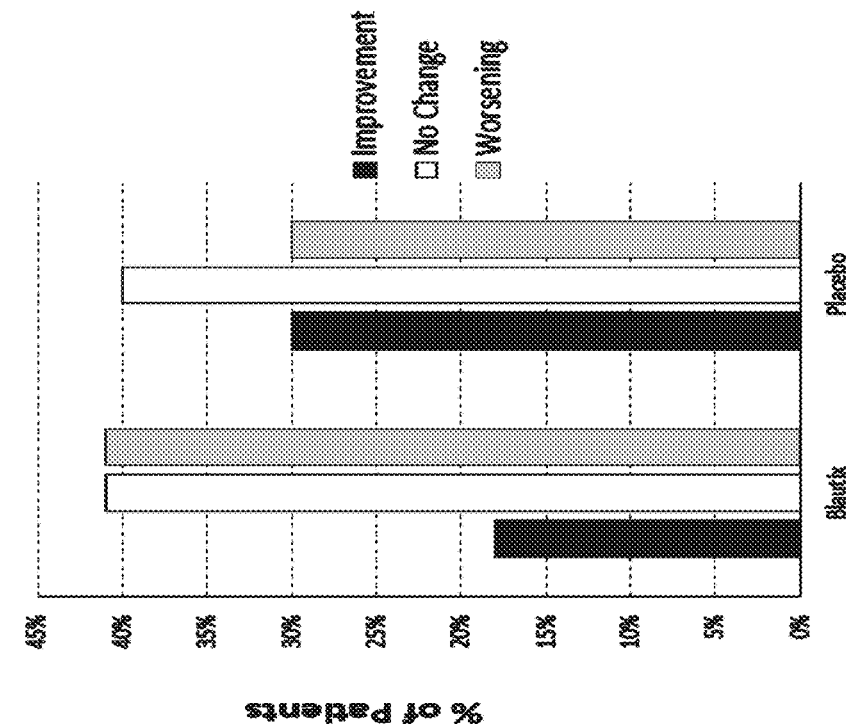
FIG. 2: Changes in patient symptoms during washout period of Phase I clinical trial.

The compositions of the invention comprise a bacterial strain of the genus *Blautia*. The examples demonstrate that bacteria of this genus are useful for treating or preventing diarrhea and/or constipation. The preferred bacterial strains are of the species *Blautia hydrogenotrophica*, *Blautia stercoris* and *Blautia wexlerae*. Other preferred bacterial strains for use in the invention are *Blautia producta*, *Blautia coccoides* and *Blautia hansenii*.

Examples of *Blautia* strains for use in the invention include *Blautia hydrogenotrophica*, *B. stercoris*, *B. faecis*, *B. coccoides*, *B. glucerasea*, *B. hansenii*, *B. luti*, *B. producta*, *B. schinkii* and *B. wexlerae*. The *Blautia* species are Gram-reaction-positive, non-motile bacteria that may be either coccoid or oval and all are obligate anaerobes that produce acetic acid as the major end product of glucose fermentation [17]. *Blautia* may be isolated from the human gut, although *B. producta* was isolated from a septicaemia sample.

*Blautia hydrogenotrophica* (previously known as *Ruminococcus hydrogenotrophicus*) has been isolated from the guts of mammals, is strictly anaerobic, and metabolises $H_2/CO_2$ to acetate, which may be important for human nutrition and health. The type strain of *Blautia hydrogenotrophica* is S5a33=DSM 10507=JCM 14656. The GenBank accession number for the 16S rRNA gene sequence of *Blautia hydrogenotrophica* strain S5a36 is X95624.1 (disclosed herein as SEQ ID NO:5). This exemplary *Blautia hydrogenotrophica* strain is described in [17] and [18]. The S5a33 strain and the S5a36 strain correspond to two subclones of a strain isolated from a faecal sample of a healthy subject. They show identical morphology, physiology and metabolism and have identical 16S rRNA sequences. Thus, in some embodiments, the *Blautia hydrogenotrophica* for use in the invention has the 16S rRNA sequence of SEQ ID NO:5.

The *Blautia hydrogenotrophica* bacterium deposited under accession number DSM 10507 and also under accession number DSM 14294 was tested in the Examples and is also referred to herein as strain BH. Strain BH was deposited with the Deutsche Sammlung von Mikroorganismen [German Microorganism Collection] (Mascheroder Weg 1b, 38124 Braunschweig, Germany) in January 1996 as "*Ruminococcus hydrogenotrophicus*" under accession number DSM 10507 and also under accession number DSM 14294 as "S5a33" on 10 May 2001. The depositor was INRA Laboratoire de Microbiologie CR de Clermont-Ferrand/Theix 63122 Saint Genes Champanelle, France. Ownership of the deposits has passed to 4D Pharma Plc by way of assignment. The DSM 14294 deposit was made under the terms of the Budapest Treaty. Maintenance of a viable culture is assured for 30 years from the date of deposit. All restrictions on the availability to the public of the microorganisms deposited as DSM 14294 and DSM 10507 will be irrevocably removed upon the granting of a patent for this application.

The GenBank accession number for the 16S rRNA gene sequence of *Blautia stercoris* strain GAM6-1$^T$ is HM626177 (disclosed herein as SEQ ID NO:1). An exemplary *Blautia stercoris* strain is described in [19]. The type strain of *Blautia wexlerae* is WAL 14507=ATCC BAA-1564=DSM 19850 [17]. The GenBank accession number for the 16S rRNA gene sequence of *Blautia wexlerae* strain WAL 14507 T is EF036467 (disclosed herein as SEQ ID NO:2). This exemplary *Blautia wexlerae* strain is described in [17].

A preferred *Blautia stercoris* strain is the strain deposited under accession number NCIMB 42381, which is also referred to herein as strain 830. A 16S rRNA sequence for the 830 strain is provided in SEQ ID NO:3. Strain 830 was deposited with the international depositary authority NCIMB, Ltd. (Ferguson Building, Aberdeen, AB21 9YA, Scotland) by GT Biologics Ltd. (Life Sciences Innovation Building, Aberdeen, AB25 2ZS, Scotland) on 12 Mar. 2015 as "*Blautia stercoris* 830" and was assigned accession number NCIMB 42381. GT Biologics Ltd. subsequently changed its name to 4D Pharma Research Limited. The NCIMB 42381 deposit was made under the terms of the Budapest Treaty. Maintenance of a viable culture is assured for 30 years from the date of deposit. All restrictions on the availability to the public of the deposited microorganism will be irrevocably removed upon the granting of a patent for this application.

A preferred *Blautia wexlerae* strain is the strain deposited under accession number NCIMB 42486, which is also referred to herein as strain MRX008. A 16S rRNA sequence for the MRX008 strain is provided in SEQ ID NO:4. Strain MRX008 was deposited with the international depositary authority NCIMB, Ltd. (Ferguson Building, Aberdeen, AB21 9YA, Scotland) by 4D Pharma Research Ltd. (Life Sciences Innovation Building, Aberdeen, AB25 2ZS, Scotland) on 16 Nov. 2015 as "*Blaqutia/Ruminococcus* MRx0008" and was assigned accession number NCIMB 424. The NCIMB 42486 deposit was made under the terms of the Budapest Treaty. Maintenance of a viable culture is assured for 30 years from the date of deposit. All restrictions on the availability to the public of the deposited microorganism will be irrevocably removed upon the granting of a patent for this application.

Bacterial strains closely related to the strain tested in the examples are also expected to be effective for treating or preventing diarrhea and/or constipation. In certain embodiments, the bacterial strain for use in the invention has a 16s rRNA sequence that is at least 95%, 96%, 97%, 98%, 99%, 99.5% or 99.9% identical to the 16s rRNA sequence of a bacterial strain of *Blautia hydrogenotrophica*. Preferably, the bacterial strain for use in the invention has a 16s rRNA sequence that is at least 95%, 96%, 97%, 98%, 99%, 99.5% or 99.9% identical to SEQ ID NO:5.

In certain embodiments, the bacterial strain for use in the invention has a 16s rRNA sequence that is at least 95%, 96%, 97%, 98%, 99%, 99.5% or 99.9% identical to the 16s rRNA sequence of a bacterial strain of *Blautia stercoris*. Preferably, the bacterial strain for use in the invention has a 16s rRNA sequence that is at least 95%, 96%, 97%, 98%, 99%, 99.5% or 99.9% identical to SEQ ID NO:1 or SEQ ID NO:3. Preferably, the sequence identity is to SEQ ID NO:3. Preferably, the bacterial strain for use in the invention has the 16s rRNA sequence represented by SEQ ID NO:3. In certain embodiments, the bacterial strain for use in the invention has a 16s rRNA sequence that is at least 95%, 96%, 97%, 98%, 99%, 99.5% or 99.9% identical to the 16s rRNA sequence of a bacterial strain of *Blautia wexlerae*. Preferably, the bacterial strain for use in the invention has a 16s rRNA sequence that is at least 95%, 96%, 97%, 98%, 99%, 99.5% or 99.9% identical to SEQ ID NO:2 or SEQ ID NO:4. Preferably, the sequence identity is to SEQ ID NO:4. Preferably, the bacterial strain for use in the invention has the 16s rRNA sequence represented by SEQ ID NO:4.

Bacterial strains that are biotypes of the bacterium deposited under accession number DSM 10507/14294 or biotypes of the bacteria deposited under accession numbers NCIMB 42381 and NCIMB 42486 are also expected to be effective for treating or preventing diarrhea and/or constipation. A biotype is a closely related strain that has the same or very similar physiological and biochemical characteristics.

Strains that are biotypes of a bacterium deposited under accession number DSM 10507/14294, NCIMB 42381 or NCIMB 42486 and that are suitable for use in the invention may be identified by sequencing other nucleotide sequences for a bacterium deposited under accession number DSM 10507/14294, NCIMB 42381 or NCIMB 42486. For example, substantially the whole genome may be sequenced and a biotype strain for use in the invention may have at least 95%, 96%, 97%, 98%, 99%, 99.5% or 99.9% sequence identity across at least 80% of its whole genome (e.g. across at least 85%, 90%, 95% or 99%, or across its whole genome). For example, in some embodiments, a biotype strain has at least 98% sequence identity across at least 98% of its genome or at least 99% sequence identity across 99% of its genome. Other suitable sequences for use in identifying biotype strains may include hsp60 or repetitive sequences such as BOX, ERIC, (GTG)$_5$, or REP or [20]. Biotype strains may have sequences with at least 95%, 96%, 97%, 98%, 99%, 99.5% or 99.9% sequence identity to the corresponding sequence of a bacterium deposited under accession number DSM 10507/14294, NCIMB 42381 or NCIMB 42486. In some embodiments, a biotype strain has a sequence with at least 97%, 98%, 99%, 99.5% or 99.9% sequence identity to the corresponding sequence of the *Blautia hydrogenotrophica* strain deposited as DSM 10507/14294 and comprises a 16S rRNA sequence that is at least 99% identical (e.g. at least 99.5% or at least 99.9% identical)

to SEQ ID NO:5. In some embodiments, a biotype strain has a sequence with at least 97%, 98%, 99%, 99.5% or 99.9% sequence identity to the corresponding sequence of the *Blautia hydrogenotrophica* strain deposited as DSM 10507/14294 and has the 16S rRNA sequence of SEQ ID NO:5.

Alternatively, strains that are biotypes of a bacterium deposited under accession number DSM 10507/14294, NCIMB 42381 or NCIMB 42486 and that are suitable for use in the invention may be identified by using the accession number DSM 10507/14294 deposit, the accession number NCIMB 42381 deposit, or the accession number NCIMB 42486 deposit, and restriction fragment analysis and/or PCR analysis, for example by using fluorescent amplified fragment length polymorphism (FAFLP) and repetitive DNA element (rep)-PCR fingerprinting, or protein profiling, or partial 16S or 23s rDNA sequencing. In preferred embodiments, such techniques may be used to identify other *Blautia hydrogenotrophica*, *Blautia stercoris* or *Blautia wexlerae* strains.

In certain embodiments, strains that are biotypes of a bacterium deposited under accession number DSM 10507/14294, NCIMB 42381 or NCIMB 42486 and that are suitable for use in the invention are strains that provide the same pattern as a bacterium deposited under accession number DSM 10507/14294, NCIMB 42381 or NCIMB 42486 when analysed by amplified ribosomal DNA restriction analysis (ARDRA), for example when using Sau3AI restriction enzyme (for exemplary methods and guidance see, for example, p11). Alternatively, biotype strains are identified as strains that have the same carbohydrate fermentation patterns as a bacterium deposited under accession number DSM 10507/14294, NCIMB 42381 or NCIMB 42486.

Other *Blautia* strains that are useful in the compositions and methods of the invention, such as biotypes of a bacterium deposited under accession number DSM 10507/14294, NCIMB 42381 or NCIMB 42486, may be identified using any appropriate method or strategy, including the assays described in the examples. For instance, strains for use in the invention may be identified by culturing bacteria and administering to rats to test in the distension assay. In particular, bacterial strains that have similar growth patterns, metabolic type and/or surface antigens to a bacterium deposited under accession number DSM 10507/14294, NCIMB 42381 or NCIMB 42486 may be useful in the invention. A useful strain will have comparable microbiota modulatory activity to the DSM 10507/14294, NCIMB 42381 or NCIMB 42486 strain. In particular, a biotype strain will elicit comparable effects on diarrhea and/or constipation to the effects shown in the Examples, which may be identified by using the culturing and administration protocols described in the Examples.

A particularly preferred strain of the invention is the *Blautia hydrogenotrophica* strain deposited under accession number DSM 10507/14294. This is the exemplary BH strain tested in the examples and shown to be effective for treating disease. Therefore, the invention provides a cell, such as an isolated cell, of the *Blautia hydrogenotrophica* strain deposited under accession number DSM 10507/14294, or a derivative thereof, for use in therapy, in particular for the diseases described herein.

A derivative of the strain deposited under accession number DSM 10507/14294, NCIMB 42381 or NCIMB 42486 may be a daughter strain (progeny) or a strain cultured (subcloned) from the original. A derivative of a strain of the invention may be modified, for example at the genetic level, without ablating the biological activity. In particular, a derivative strain of the invention is therapeutically active. A derivative strain will have comparable microbiota modulatory activity to the original DSM 10507/14294, NCIMB 42381 or NCIMB 42486 strain. In particular, a derivative strain will elicit comparable effects on diarrhea and/or constipation to the effects shown in the Examples, which may be identified by using the culturing and administration protocols described in the Examples. A derivative of the DSM 10507/14294 strain will generally be a biotype of the DSM 10507/14294 strain. A derivative of the NCIMB 42381 strain will generally be a biotype of the NCIMB 42381 strain. A derivative of the NCIMB 42486 strain will generally be a biotype of the NCIMB 42486 strain.

References to cells of the *Blautia hydrogenotrophica* strain deposited under accession number DSM 10507/14294 encompass any cells that have the same safety and therapeutic efficacy characteristics as the strains deposited under accession number DSM 10507/14294, and such cells are encompassed by the invention. References to cells of the *Blautia stercoris* strain deposited under accession number NCIMB 42381 encompass any cells that have the same safety and therapeutic efficacy characteristics as the strains deposited under accession number NCIMB 42381, and such cells are encompassed by the invention. References to cells of the *Blautia wexlerae* strain deposited under accession number NCIMB 42486 encompass any cells that have the same safety and therapeutic efficacy characteristics as the strains deposited under accession number NCIMB 42486, and such cells are encompassed by the invention.

In preferred embodiments, the bacterial strains in the compositions of the invention are viable and capable of partially or totally colonising the intestine.

Therapeutic Uses

In preferred embodiments, the compositions of the invention are for use in treating diarrhea and/or constipation. In some embodiments the composition is for use in treating a patient having both diarrhea and constipation. In some embodiments the composition is for use in treating a patient having diarrhea without constipation. In some embodiments the composition is for use in treating a patient having constipation without diarrhea. Although patients often exhibit either diarrhea or constipation, a single patient may exhibit both conditions at different times. Patients having IBS and/or inflammatory diseases of the intestine often exhibit diarrhea and/or constipation. Accordingly, the invention provides the composition of the invention for use in treating a patient diagnosed with or suspected of having IBS or an inflammatory disease of the intestine. For example, IBS patients may experience alternating cycles of diarrhea and constipation or an IBS patient may be characterised as an IBS patient with diarrhea or an IBS patient with constipation. In some embodiments, a composition of the invention may be used to treat a patient having IBS, a patient having IBS with diarrhea or a patient having IBS with constipation. For example, in some embodiments, the subject diagnosed with IBS has IBS with both diarrhea and constipation. In some embodiments, the subject diagnosed with IBS has IBS with diarrhea but without constipation or with only a small amount of constipation. In some embodiments, the subject diagnosed with IBS has IBS with constipation but without diarrhea or with only a small amount of diarrhea. In some embodiments, the inflammatory disease is of the small intestine, colon or rectum. Diarrhea is a symptom of Crohn's disease and ulcerative colitis. Accordingly, a composition of the invention may be used to treat a patient having Crohn's disease or ulcerative colitis.

As demonstrated in the examples, bacterial compositions of the invention may be effective for reducing diarrhea and/or constipation.

In preferred embodiments, the compositions of the invention are for use in treating or preventing diarrhea and/or constipation associated with Crohn's disease, ulcerative colitis or, more preferably, IBS. In preferred embodiments, the compositions of the invention are for use in treating or preventing diarrhea and/or constipation in a subject diagnosed with Crohn's disease, ulcerative colitis or, more preferably, IBS. In preferred embodiments the compositions of the invention are for use in treating or preventing diarrhea and/or constipation in the treatment of Crohn's disease, ulcerative colitis or, more preferably, IBS. In some embodiments, the patient has abdominal pain and/or bloating in addition to diarrhea and/or constipation. In such embodiments, the patient may have any combination of two, three or all four of these conditions. For example, the patient may have diarrhea, constipation, abdominal pain and bloating; diarrhea, constipation and abdominal pain; diarrhea, constipation and bloating; diarrhea, abdominal pain and/or bloating without constipation; constipation, abdominal pain and/or bloating without diarrhea.

In certain embodiments, the composition may be in the form of a bacterial culture. In some embodiments, the composition may preferably be a lyophilisate.

In some embodiments, the composition of the invention is for use in treating diarrhea and/or constipation in a subject having an increased level of hydrogen in their breath relative to a healthy subject. In some embodiments, the composition of the invention is for use in reducing the hydrogen level in the breath of a subject having diarrhea and/or constipation. The subject is preferably a subject diagnosed as having IBS and/or an inflammatory disease of the intestine. In some embodiments, the inflammatory disease is of the small intestine, colon or rectum. In some embodiments, the subject has been diagnosed with Crohn's disease, ulcerative colitis or, more preferably, IBS, for example one of the types of IBS described herein. Without being bound by theory, it is speculated that the increased hydrogen level arises from the mechanisms underlying the inflammation in the intestine. The examples show that treatment with a composition of the invention reduces the level of hydrogen detected in hydrogen breath tests. Accordingly, the hydrogen levels are preferably assessed using a hydrogen breath test. The hydrogen breath test is well known in the art and so the skilled person will know how to conduct such a test. In some embodiments, the patient is administered lactulose as the substrate for the test.

The hydrogen breath test is also a useful tool for monitoring the effectiveness or likely effectiveness of treatment or prevention using a composition of an invention. For example, a reduction in the level of hydrogen detected in a subject's breath following treatment or prevention by a composition of the invention may indicate that the treatment is having a therapeutic or preventative effect. Accordingly, in some embodiments the methods and uses of the invention further comprise monitoring the hydrogen level in a subject's breath during and/or following treatment or prevention with a composition of the invention and thereby assessing the effectiveness or likely effectiveness of treatment or prevention. For example, hydrogen levels may be monitored at one or more (e.g. 1, 2, 3, 4 or more than 4) times, for example, including before treatment, at the start of treatment, during treatment, at the end of treatment and/or following treatment, as desired. In some embodiments, the level of hydrogen in the subject's breath at the end and/or following the dosing period (during which the composition is administered to the subject) is compared to the level at the start and/or before the dosing period and a reduction in the level indicates the effectiveness or likely effectiveness of the treatment or prevention. For example, in embodiments in which the dosing period is 16 days, it may be desirable to take measurements at day 1 and day 16, or for example at day 1, day 2, day 15 and day 16. In some embodiments, multiple measurements are taken and the mean of those measurements obtained (for example, the mean of day 1 and day 2 and the mean of day 15 and day 16). In some embodiments, a reduction in at least 40 ppm in the hydrogen level Cmax indicates that the treatment or prevention is effective or likely to be effective. In some embodiments, the hydrogen level in the subject's breath is measured only once, for example, at the end of or following treatment, and the finding that the level is at or close to a predetermined level is indicative that the treatment or prevention is likely to have been effective. The hydrogen breath test is a standard assay and so predetermined levels are known in the art.

In certain embodiments, the compositions of the invention are for use in preventing diarrhea and/or constipation in a subject that is receiving or has received or is about to receive (for example, later the same day, the next day, or within 2, 3, 4, 5, 6, 7, 10, 14 or 21 days) antibiotic treatment or that is suffering from or has suffered from bacterial gastroenteritis. Antibiotic treatment and bacterial gastroenteritis are associated with changes in the gut microbiota that may precede diarrhea and/or constipation and that may be prevented by the compositions of the invention. The compositions of the invention may be administered simultaneously, separately or sequentially with an antibiotic treatment. For example, the compositions of the invention may be administered concurrently with an antibiotic treatment.

In preferred embodiments, treatment with compositions of the invention results in a reduction in diarrhea and/or constipation.

Treatment or prevention of diarrhea and/or constipation may refer to, for example, an alleviation of the severity of symptoms or a reduction in the frequency of exacerbations or the range of triggers that are a problem for the patient.

In certain embodiments, the compositions of the invention are for use in treating or preventing a disease associated with Enterobacteriaceae infection, such as *E. coli* infection. In certain embodiments, the compositions of the invention are for use in treating or preventing diarrhea, gastroenteritis, urinary tract infection or neonatal meningitis. In such embodiments the Enterobacteriaceae may be a pathogenic strain.

In certain embodiments, the compositions of the invention are for use in treating or preventing a disease associated with increased levels of Enterobacteriaceae, such as *E. coli*. In certain embodiments, the compositions of the invention are for use in treating or preventing diarrhea, gastroenteritis, urinary tract infection or neonatal meningitis. In such embodiments, the Enterobacteriaceae may be a commensal or non-pathogenic strain.

In preferred embodiments, the compositions of the invention are for use in reducing the level of Enterobacteriaceae in the gastrointestinal tract, preferably the level of *E. coli*, in the treatment or prevention of a disease associated with increased levels of Enterobacteriaceae, such as IBS, Crohn's disease, ulcerative colitis, functional dyspepsia, diarrhea, gastroenteritis, urinary tract infection or neonatal meningitis. Enterobacteriaceae and in particular *E. coli* are known to be potential triggers for, or known to exacerbate, Crohn's disease and ulcerative colitis [22-24], so the effect shown in the examples for the compositions of the invention may be beneficial in the treatment of these conditions.

In certain embodiments, the compositions of the invention are for use in treating or preventing IBS, Crohn's disease, ulcerative colitis, functional dyspepsia, diarrhea, gastroenteritis, urinary tract infection or neonatal meningitis by reducing the level of Enterobacteriaceae in the gastrointestinal tract.

Modes of administration Preferably, the compositions of the invention are to be administered to the gastrointestinal tract in order to enable delivery to and/or partial or total colonisation of the intestine with the bacterial strain of the invention. Generally, the compositions of the invention are administered orally, but they may be administered rectally, intranasally, or via buccal or sublingual routes.

In certain embodiments, the compositions of the invention may be administered as a foam, as a spray or a gel.

In certain embodiments, the compositions of the invention may be administered as a suppository, such as a rectal suppository, for example in the form of a *theobroma* oil (cocoa butter), synthetic hard fat (e.g. suppocire, witepsol), glycero-gelatin, polyethylene glycol, or soap glycerin composition.

In certain embodiments, the composition of the invention is administered to the gastrointestinal tract via a tube, such as a nasogastric tube, orogastric tube, gastric tube, jejunostomy tube (J tube), percutaneous endoscopic gastrostomy (PEG), or a port, such as a chest wall port that provides access to the stomach, jejunum and other suitable access ports.

The compositions of the invention may be administered once, or they may be administered sequentially as part of a treatment regimen. In certain embodiments, the compositions of the invention are to be administered daily. The examples demonstrate that administration provides successful colonisation and clinical benefits in treatment of diarrhea and/or constipation.

In certain embodiments, the compositions of the invention are administered regularly, such as daily, every two days, or weekly, for an extended period of time, such as for at least one week, two weeks, one month, two months, six months, or one year. The examples demonstrate that BH administration may not result in permanent colonisation of the intestines, so regular administration for extended periods of time may provide greater therapeutic benefits.

In some embodiments the compositions of the invention are administered for 7 days, 14 days, 16 days, 21 days or 28 days or no more than 7 days, 14 days, 16 days, 21 days or 28 days. For example, in some embodiments the compositions of the invention are administered for 16 days.

In certain embodiments of the invention, treatment according to the invention is accompanied by assessment of the patient's gut microbiota. Treatment may be repeated if delivery of and/or partial or total colonisation with the strain of the invention is not achieved such that efficacy is not observed, or treatment may be ceased if delivery and/or partial or total colonisation is successful and efficacy is observed.

In certain embodiments, the composition of the invention may be administered to a pregnant animal, for example a mammal such as a human in order to prevent diarrhea and/or constipation developing in her child in utero and/or after it is born.

The compositions of the invention may be administered to a patient that has been diagnosed with diarrhea and/or constipation or a disease or condition associated with diarrhea and/or constipation, or that has been identified as being at risk of diarrhea and/or constipation. The compositions may also be administered as a prophylactic measure to prevent the development of diarrhea and/or constipation in a healthy patient.

The compositions of the invention may be administered to a patient that has been identified as having an abnormal gut microbiota. For example, the patient may have reduced or absent colonisation by *Blautia*, and in particular *Blautia hydrogenotrophica, Blautia stercoris* or *Blautia wexlerae.*

The compositions of the invention may be administered as a food product, such as a nutritional supplement.

Generally, the compositions of the invention are for the treatment of humans, although they may be used to treat animals including monogastric mammals such as poultry, pigs, cats, dogs, horses or rabbits. The compositions of the invention may be useful for enhancing the growth and performance of animals. If administered to animals, oral gavage may be used.

In some embodiments, the subject to whom the composition is to be administered is an adult human.

In some embodiments, the subject to whom the composition is to be administered is an infant human.

Compositions

Generally, the composition of the invention comprises bacteria. In preferred embodiments of the invention, the composition is formulated in freeze-dried form. For example, the composition of the invention may comprise granules or gelatin capsules, for example hard gelatin capsules, comprising a bacterial strain of the invention.

Preferably, the composition of the invention comprises lyophilised bacteria. Lyophilisation of bacteria is a well-established procedure and relevant guidance is available in, for example, references [25-27] Lyophilisate compositions may be particularly effective. In preferred embodiments, the compositions of the invention comprises lyophilised bacteria and is for the treatment of diarrhea and/or constipation associated with IBS.

Alternatively, the composition of the invention may comprise a live, active bacterial culture. The examples demonstrate that cultures of the bacteria of the invention are therapeutically effective.

In some embodiments, the bacterial strain in the composition of the invention has not been inactivated, for example, has not been heat-inactivated. In some embodiments, the bacterial strain in the composition of the invention has not been killed, for example, has not been heat-killed. In some embodiments, the bacterial strain in the composition of the invention has not been attenuated, for example, has not been heat-attenuated. For example, in some embodiments, the bacterial strain in the composition of the invention has not been killed, inactivated and/or attenuated. For example, in some embodiments, the bacterial strain in the composition of the invention is live. For example, in some embodiments, the bacterial strain in the composition of the invention is viable. For example, in some embodiments, the bacterial strain in the composition of the invention is capable of partially or totally colonising the intestine. For example, in some embodiments, the bacterial strain in the composition of the invention is viable and capable of partially or totally colonising the intestine.

In some embodiments, the composition comprises a mixture of live bacterial strains and bacterial strains that have been killed.

In preferred embodiments, the composition of the invention is encapsulated to enable delivery of the bacterial strain to the intestine. Encapsulation protects the composition from degradation until delivery at the target location through, for example, rupturing with chemical or physical stimuli such as pressure, enzymatic activity, or physical disintegration, which may be triggered by changes in pH. Any appropriate encapsulation method may be used. Exemplary encapsulation techniques include entrapment within a porous matrix, attachment or adsorption on solid carrier surfaces, self-aggregation by flocculation or with cross-linking agents, and mechanical containment behind a microporous membrane or a microcapsule. Guidance on encapsulation that may be useful for preparing compositions of the invention is available in, for example, references [28-29].

The composition may be administered orally and may be in the form of a tablet, capsule or powder. Encapsulated products are preferred because *Blautia* are anaerobes. Other ingredients (such as vitamin C, for example), may be included as oxygen scavengers and prebiotic substrates to improve the delivery and/or partial or total colonisation and survival in vivo. Alternatively, the probiotic composition of the invention may be administered orally as a food or nutritional product, such as milk or whey based fermented dairy product, or as a pharmaceutical product.

The composition may be formulated as a probiotic.

A composition of the invention includes a therapeutically effective amount of a bacterial strain of the invention. A therapeutically effective amount of a bacterial strain is sufficient to exert a beneficial effect upon a patient. A therapeutically effective amount of a bacterial strain may be sufficient to result in delivery to and/or partial or total colonisation of the patient's intestine.

A suitable daily dose of the bacteria, for example for an adult human, may be from about $1\times10^3$ to about $1\times10^{11}$ colony forming units (CFU); for example, from about $1\times10^7$ to about $1\times10^{10}$ CFU; in another example from about $1\times10^6$ to about $1\times10^{10}$ CFU; in another example from about $1\times10^7$ to about $1\times10^{11}$ CFU; in another example from about $1\times10^8$ to about $1\times10^{10}$ CFU; in another example from about $1\times10^8$ to about $1\times10^{11}$ CFU.

In certain embodiments, the dose of the bacteria is at least $10^9$ cells per day, such as at least $10^{10}$, at least $10^{11}$, or at least $10^{12}$ cells per day.

In certain embodiments, the composition contains the bacterial strain in an amount of from about $1\times10^6$ to about $1\times10^{11}$ CFU/g, respect to the weight of the composition; for example, from about $1\times10^8$ to about $1\times10^{10}$ CFU/g. The dose may be, for example, 1 g, 3 g, 5 g, and 10 g.

Typically, a probiotic, such as the composition of the invention, is optionally combined with at least one suitable prebiotic compound. A prebiotic compound is usually a non-digestible carbohydrate such as an oligo- or polysaccharide, or a sugar alcohol, which is not degraded or absorbed in the upper digestive tract. Known prebiotics include commercial products such as inulin and transgalacto-oligosaccharides.

In certain embodiments, the probiotic composition of the present invention includes a prebiotic compound in an amount of from about 1 to about 30% by weight, respect to the total weight composition, (e.g. from 5 to 20% by weight). Carbohydrates may be selected from the group consisting of: fructo-oligosaccharides (or FOS), short-chain fructo-oligosaccharides, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. In one aspect, the prebiotics are the short-chain fructo-oligosaccharides (for simplicity shown herein below as FOSs-c.c); said FOSs-c.c. are not digestible carbohydrates, generally obtained by the conversion of the beet sugar and including a saccharose molecule to which three glucose molecules are bonded.

The compositions of the invention may comprise pharmaceutically acceptable excipients or carriers. Examples of such suitable excipients may be found in the reference [30]. Acceptable carriers or diluents for therapeutic use are well known in the pharmaceutical art and are described, for example, in reference [31]. Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid, cysteine and esters of p-hydroxybenzoic acid, for example, in some embodiments the preservative is selected from sodium benzoate, sorbic acid and esters of p-hydroxybenzoic acid. Antioxidants and suspending agents may be also used. A further example of a suitable carrier is saccharose. A further example of a preservative is cysteine.

The compositions of the invention may be formulated as a food product. For example, a food product may provide nutritional benefit in addition to the therapeutic effect of the invention, such as in a nutritional supplement. Similarly, a food product may be formulated to enhance the taste of the composition of the invention or to make the composition more attractive to consume by being more similar to a common food item, rather than to a pharmaceutical composition. In certain embodiments, the composition of the invention is formulated as a milk-based product. The term "milk-based product" means any liquid or semi-solid milk- or whey-based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavoured milks, ice cream; milk-containing food such as sweets.

In some embodiments, the compositions of the invention comprise one or more bacterial strains of the genus *Blautia* and do not contain bacteria from any other genus, or which comprise only de minimis or biologically irrelevant amounts of bacteria from another genus.

In certain embodiments, the compositions of the invention contain a single bacterial strain or species and do not contain any other bacterial strains or species. Such compositions may comprise only de minimis or biologically irrelevant amounts of other bacterial strains or species. Such compositions may be a culture that is substantially free from other species of organism. In some embodiments, such compositions may be a lyophilisate that is substantially free from other species of organism.

In certain embodiments, the compositions of the invention comprise one or more bacterial strains of the genus *Blautia*, for example, a *Blautia hydrogenotrophica*, and do not contain any other bacterial genus, or which comprise only de minimis or biologically irrelevant amounts of bacteria from another genus. In certain embodiments, the compositions of the invention comprise a single species of *Blautia*, for example, a *Blautia hydrogenotrophica*, and do not contain any other bacterial species, or which comprise only de minimis or biologically irrelevant amounts of bacteria from another species. In certain embodiments, the compositions of the invention comprise a single strain of *Blautia*, for example, of *Blautia hydrogenotrophica*, and do not contain any other bacterial strains or species, or which comprise only de minimis or biologically irrelevant amounts of bacteria from another strain or species.

In some embodiments, the compositions of the invention comprise more than one bacterial strain or species. For example, in some embodiments, the compositions of the invention comprise more than one strain from within the same species (e.g. more than 1, 2, 3, 4, 5, 6, 7, 8, 9, 10, 15, 20, 25, 30, 35, 40 or 45 strains), and, optionally, do not contain bacteria from any other species. In some embodiments, the compositions of the invention comprise less than 50 strains from within the same species (e.g. less than 45, 40, 35, 30, 25, 20, 15, 12, 10, 9, 8, 7, 6, 5, 4 or 3 strains), and, optionally, do not contain bacteria from any other species. In some embodiments, the compositions of the invention comprise 1-40, 1-30, 1-20, 1-19, 1-18, 1-15, 1-10, 1-9, 1-8, 1-7, 1-6, 1-5, 1-4, 1-3, 1-2, 2-50, 2-40, 2-30, 2-20, 2-15, 2-10, 2-5, 6-30, 6-15, 16-25, or 31-50 strains from within the same species and, optionally, do not contain bacteria from any other species. In some embodiments, the compositions of the invention comprise more than one species from within the same genus (e.g. more than 1, 2, 3, 4, 5, 6, 7, 8, 9, 10, 12, 15, 17, 20, 23, 25, 30, 35 or 40 species), and, optionally, do not contain bacteria from any other genus. In some embodiments, the compositions of the invention comprise less than 50 species from within the same genus (e.g. less than 50, 45, 40, 35, 30, 25, 20, 15, 12, 10, 8, 7, 6, 5, 4 or 3 species), and, optionally, do not contain bacteria from any other genus.

In some embodiments, the compositions of the invention comprise 1-50, 1-40, 1-30, 1-20, 1-15, 1-10, 1-9, 1-8, 1-7, 1-6, 1-5, 1-4, 1-3, 1-2, 2-50, 2-40, 2-30, 2-20, 2-15, 2-10, 2-5, 6-30, 6-15, 16-25, or 31-50 species from within the same genus and, optionally, do not contain bacteria from any other genus. The invention comprises any combination of the foregoing.

In some embodiments, the composition comprises a microbial consortium. For example, in some embodiments, the composition comprises the *Blautia* bacterial strain as part of a microbial consortium. For example, in some embodiments, the *Blautia* bacterial strain is present in combination with one or more (e.g. at least 2, 3, 4, 5, 10, 15 or 20) other bacterial strains from other genera with which it can live symbiotically in vivo in the intestine. For example, in some embodiments, the composition comprises a bacterial strain of *Blautia hydrogenotrophica* in combination with a bacterial strain from a different genus. In some embodiments, the microbial consortium comprises two or more bacterial strains obtained from a faeces sample of a single organism, e.g. a human. In some embodiments, the microbial consortium is not found together in nature. For example, in some embodiments, the microbial consortium comprises bacterial strains obtained from faeces samples of at least two different organisms. In some embodiments, the two different organisms are from the same species, e.g. two different humans. In some embodiments, the two different organisms are an infant human and an adult human. In some embodiments, the two different organisms are a human and a non-human mammal.

In some embodiments, the composition of the invention additionally comprises a bacterial strain that has the same safety and therapeutic efficacy characteristics as the *Blautia hydrogenotrophica* strain deposited under accession number DSM 10507/14294, but which is not the *Blautia hydrogenotrophica* strain deposited under accession number DSM 10507/14294, or which is not a *Blautia hydrogenotrophica* or which is not a *Blautia*.

In some embodiments in which the composition of the invention comprises more than one bacterial strain, species or genus, the individual bacterial strains, species or genera may be for separate, simultaneous or sequential administration. For example, the composition may comprise all of the more than one bacterial strain, species or genera, or the bacterial strains, species or genera may be stored separately and be administered separately, simultaneously or sequentially. In some embodiments, the more than one bacterial strains, species or genera are stored separately but are mixed together prior to use.

In some embodiments, the bacterial strain for use in the invention is obtained from human adult faeces. In some embodiments in which the composition of the invention comprises more than one bacterial strain, all of the bacterial strains are obtained from human adult faeces or if other bacterial strains are present they are present only in de minimis amounts. The bacteria may have been cultured subsequent to being obtained from the human adult faeces and being used in a composition of the invention.

In some embodiments, the one or more *Blautia* bacterial strains is/are the only therapeutically active agent(s) in a composition of the invention. In some embodiments, the bacterial strain(s) in the composition is/are the only therapeutically active agent(s) in a composition of the invention.

The compositions for use in accordance with the invention may or may not require marketing approval.

In certain embodiments, the invention provides the above pharmaceutical composition, wherein said bacterial strain is lyophilised. In certain embodiments, the invention provides the above pharmaceutical composition, wherein said bacterial strain is spray dried. In certain embodiments, the invention provides the above pharmaceutical composition, wherein the bacterial strain is lyophilised or spray dried and wherein it is live. In certain embodiments, the invention provides the above pharmaceutical composition, wherein the bacterial strain is lyophilised or spray dried and wherein it is viable. In certain embodiments, the invention provides the above pharmaceutical composition, wherein the bacterial strain is lyophilised or spray dried and wherein it is capable of partially or totally colonising the intestine. In certain embodiments, the invention provides the above pharmaceutical composition, wherein the bacterial strain is lyophilised or spray dried and wherein it is viable and capable of partially or totally colonising the intestine.

In some cases, the lyophilised or spray dried bacterial strain is reconstituted prior to administration. In some cases, the reconstitution is by use of a diluent described herein.

The compositions of the invention can comprise pharmaceutically acceptable excipients, diluents or carriers.

In certain embodiments, the invention provides a pharmaceutical composition comprising: a bacterial strain of the invention; and a pharmaceutically acceptable excipient, carrier or diluent; wherein the bacterial strain is in an amount sufficient to treat a disorder when administered to a subject in need thereof; and wherein the disorder is diarrhea and/or constipation, such as diarrhea and/or constipation associated with Crohn's disease, ulcerative colitis or, more preferably, IBS.

In certain embodiments, the invention provides the above pharmaceutical composition, wherein the amount of the bacterial strain is from about $1 \times 10^3$ to about $1 \times 10^{11}$ colony forming units per gram with respect to a weight of the composition.

In certain embodiments, the invention provides the above pharmaceutical composition, wherein the composition is administered at a dose of 1 g, 3 g, 5 g or 10 g.

In certain embodiments, the invention provides the above pharmaceutical composition, wherein the composition is administered by a method selected from the group consisting of oral, rectal, subcutaneous, nasal, buccal, and sublingual.

In certain embodiments, the invention provides the above pharmaceutical composition, comprising a carrier selected from the group consisting of lactose, starch, glucose, methyl cellulose, magnesium stearate, mannitol and sorbitol.

In certain embodiments, the invention provides the above pharmaceutical composition, comprising a diluent selected from the group consisting of ethanol, glycerol and water.

In certain embodiments, the invention provides the above pharmaceutical composition, comprising an excipient selected from the group consisting of starch, gelatin, glucose, anhydrous lactose, free-flow lactose, beta-lactose, corn sweetener, acacia, tragacanth, sodium alginate, carboxymethyl cellulose, polyethylene glycol, sodium oleate, sodium stearate, magnesium stearate, sodium benzoate, sodium acetate and sodium chloride.

In certain embodiments, the invention provides the above pharmaceutical composition, further comprising at least one of a preservative, an antioxidant and a stabilizer.

In certain embodiments, the invention provides the above pharmaceutical composition, comprising a preservative selected from the group consisting of sodium benzoate, sorbic acid and esters of p-hydroxybenzoic acid.

In certain embodiments, there is provided the pharmaceutical composition of the invention, wherein the composition does not comprise any minerals, or more specifically, does not comprise any metals with an atomic number greater than 33, for example, wherein the composition does not comprise any minerals from the group consisting of selenium, molybdenum, tungsten, selenium compounds, molybdenum compounds and tungsten compounds.

In certain embodiments, the invention provides the above pharmaceutical composition, wherein said bacterial strain is lyophilised.

In certain embodiments, the invention provides the above pharmaceutical composition, wherein when the composition is stored in a sealed container at about 4.0 or about 25.0 and the container is placed in an atmosphere having 50% relative humidity, at least 80% of the bacterial strain as measured in colony forming units, remains after a period of at least about: 1 month, 3 months, 6 months, 1 year, 1.5 years, 2 years, 2.5 years or 3 years.

In some embodiments, the composition of the invention is provided in a sealed container comprising a composition as described herein. In some embodiments, the sealed container is a sachet or bottle. In some embodiments, the composition of the invention is provided in a syringe comprising a composition as described herein.

The composition of the present invention may, in some embodiments, be provided as a pharmaceutical formulation. For example, the composition may be provided as a tablet or capsule. In some embodiments, the capsule is a gelatine capsule ("gel-cap").

In some embodiments, the compositions of the invention are administered orally. Oral administration may involve swallowing, so that the compound enters the gastrointestinal tract, and/or buccal, lingual, or sublingual administration by which the compound enters the blood stream directly from the mouth.

Pharmaceutical formulations suitable for oral administration include solid plugs, solid microparticulates, semi-solid and liquid (including multiple phases or dispersed systems) such as tablets; soft or hard capsules containing multi- or nano-particulates, liquids (e.g. aqueous solutions), emulsions or powders; lozenges (including liquid-filled); chews; gels; fast dispersing dosage forms; films; ovules; sprays; and buccal/mucoadhesive patches.

In some embodiments the pharmaceutical formulation is an enteric formulation, i.e. a gastro-resistant formulation (for example, resistant to gastric pH) that is suitable for delivery of the composition of the invention to the intestine by oral administration. Enteric formulations may be particularly useful when the bacteria or another component of the composition is acid-sensitive, e.g. prone to degradation under gastric conditions.

In some embodiments, the enteric formulation comprises an enteric coating. In some embodiments, the formulation is an enteric-coated dosage form. For example, the formulation may be an enteric-coated tablet or an enteric-coated capsule, or the like. The enteric coating may be a conventional enteric coating, for example, a conventional coating for a tablet, capsule, or the like for oral delivery. The formulation may comprise a film coating, for example, a thin film layer of an enteric polymer, e.g. an acid-insoluble polymer.

In some embodiments, the enteric formulation is intrinsically enteric, for example, gastro-resistant without the need for an enteric coating. Thus, in some embodiments, the formulation is an enteric formulation that does not comprise an enteric coating. In some embodiments, the formulation is a capsule made from a thermogelling material. In some embodiments, the thermogelling material is a cellulosic material, such as methylcellulose, hydroxymethylcellulose or hydroxypropylmethylcellulose (HPMC). In some embodiments, the capsule comprises a shell that does not contain any film forming polymer. In some embodiments, the capsule comprises a shell and the shell comprises hydroxypropylmethylcellulose and does not comprise any film forming polymer (e.g. see [32]). In some embodiments, the formulation is an intrinsically enteric capsule (for example, Vcaps® from Capsugel).

In some embodiments, the formulation is a soft capsule. Soft capsules are capsules which may, owing to additions of softeners, such as, for example, glycerol, sorbitol, maltitol and polyethylene glycols, present in the capsule shell, have a certain elasticity and softness. Soft capsules can be produced, for example, on the basis of gelatine or starch. Gelatine-based soft capsules are commercially available from various suppliers. Depending on the method of administration, such as, for example, orally or rectally, soft capsules can have various shapes, they can be, for example, round, oval, oblong or torpedo-shaped. Soft capsules can be produced by conventional processes, such as, for example, by the Scherer process, the Accogel process or the droplet or blowing process.

Culturing Methods

The bacterial strains for use in the present invention can be cultured using standard microbiology techniques as detailed in, for example, references [33-35].

The solid or liquid medium used for culture may for example be YCFA agar or YCFA medium. YCFA medium may include (per 100 ml, approximate values): Casitone (1.0 g), yeast extract (0.25 g), NaHCO$_3$ (0.4 g), cysteine (0.1 g), K$_2$HPO$_4$ (0.045 g), KH$_2$PO$_4$ (0.045 g), NaCl (0.09 g), (NH$_4$)$_2$SO$_4$ (0.09 g), MgSO$_4$.7H$_2$O (0.009 g), CaCl$_2$ (0.009 g), resazurin (0.1 mg), hemin (1 mg), biotin (1 µg), cobalamin (1 µg), p-aminobenzoic acid (3 µg), folic acid (5 µg), and pyridoxamine (15 µg).

General

The practice of the present invention will employ, unless otherwise indicated, conventional methods of chemistry, biochemistry, molecular biology, immunology and pharmacology, within the skill of the art. Such techniques are explained fully in the literature. See, e.g., references [36-43], etc.

The term "comprising" encompasses "including" as well as "consisting" e.g. a composition "comprising" X may consist exclusively of X or may include something additional e.g. X+Y.

The term "about" in relation to a numerical value x is optional and means, for example, x+10%.

The word "substantially" does not exclude "completely" e.g. a composition which is "substantially free" from Y may be completely free from Y. Where necessary, the word "substantially" may be omitted from the definition of the invention.

References to a percentage sequence identity between two nucleotide sequences means that, when aligned, that percentage of nucleotides are the same in comparing the two sequences. This alignment and the percent homology or sequence identity can be determined using software programs known in the art, for example those described in section 7.7.18 of ref [44]. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref [45].

Unless specifically stated, a process or method comprising numerous steps may comprise additional steps at the beginning or end of the method, or may comprise additional intervening steps. Also, steps may be combined, omitted or performed in an alternative order, if appropriate.

Various embodiments of the invention are described herein. It will be appreciated that the features specified in each embodiment may be combined with other specified features, to provide further embodiments. In particular, embodiments highlighted herein as being suitable, typical or preferred may be combined with each other (except when they are mutually exclusive).

MODES FOR CARRYING OUT THE INVENTION

Example 1—Changes in Patient Symptoms During Phase I Clinical Trial

A Phase I clinical trial was conducted in which *Blautia hydrogenotrophica* ("Blautix", strain deposited under accession number DSM 10507 and also under accession number DSM 14294) was administered to human patients having irritable bowel syndrome (IBS). Patients were administered Blautix during a dosing period (days 1-16) with the washout period being day 19-23. Blautix was found to be both safe and well tolerated. Four symptoms were monitored, of which two were diarrhea and constipation. The study recorded whether patients experienced an improvement in, no change in or worsening of each of these symptoms. Results from patients administered Blautix were compared with those obtained using patients administered a placebo. Symptoms were monitored at three time points: day 1, day 15/16 and at the end of the study. The results are shown in FIGS. 1 and 2.

Figure 1:
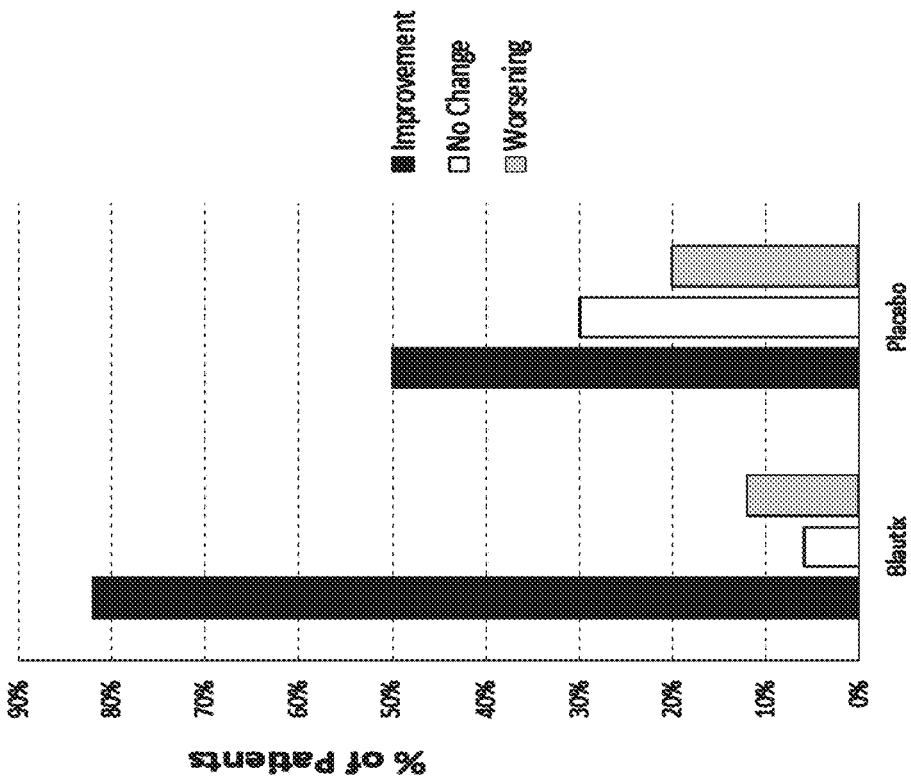
FIG. 1: Changes in patient symptoms during dosing period (days 1-16) of Phase I clinical trial.

When the patients' reported symptoms at day 16 were compared to the baseline from day 1, 82% of 17 IBS patients receiving Blautix reported an improvement in symptoms (FIG. 1). Improvement of symptoms, two of which are diarrhea and constipation, supports the use of Blautix for treating or preventing diarrhea and/or constipation.

50% of patients receiving placebo reported an improvement in symptoms (FIG. 1). High placebo response rates are an established phenomenon in IBS clinical studies. Xifaxan was recently approved to treat IBS based on much smaller improvements over placebo (see: http://www.accessdata.fda.gov/spl/data/5ab6fceb-4d22-4480-81fc-8bc28c16770d/5ab6fceb-4d22-4480-81fc-8bc28c16770d.xml).

A worsening of symptoms at the study completion (day 19-23) compared to symptoms present upon dosing completion (day 16) is expected based on the teaching presented here. This worsening of symptoms was seen in the Phase I clinical trial: 41% of IBS patients reported worsening of symptoms following cessation of Blautix dosing (FIG. 2). The worsening of symptoms, two of which are diarrhea and constipation, following cessation of Blautix dosing therefore also supports the use of Blautix in treating or preventing diarrhea and/or constipation.

Example 2—Hydrogen Breath Test Results

Breath hydrogen levels are a biomarker of Blautix activity—MoA involves metabolism of endogenous H$_2$ to produce acetate. Human subjects were administered lactulose and hydrogen (H$_2$) levels (Cmax) were sampled at four time points: day 1, day 2, day 15 and day 16. Hydrogen uncorrected results were converted to hydrogen corrected results.

Some patients were excluded from the analysis. There were three reasons why a subject was not included in the hydrogen breath test analysis: 1) They produced a CMAX hydrogen breath test result of <20 on one of the four sampling days and were therefore deemed to have not responded to the test; 2) They were methane producers (taken as producing more methane than hydrogen in the breath test), this affects the hydrogen response; and/or 3) there was an aberrant value obtained in the hydrogen breath test (232 ppm). Subjects 3.12 (Blautix), 3.24 (Blautix), 4.07 (Blautix) were excluded as non-responders. Subjects 3.03 (Blautix) and 3.08 (Placebo) were excluded as methane producers (4.07, mentioned as excluded above, was also a methane producer). Subject 4.09 (Placebo) was excluded due to an aberrant value.

The results of the corrected hydrogen analysis from the end of the dosing period (day 15/16) were compared to those from the baseline (day ½). 10 out of 12 patients (83%) receiving Blautix had a reduction in hydrogen levels over this period (FIGS. 3a and 3c). In contrast, 3 out of 6 (50%) patients receiving placebo had reduced hydrogen levels (FIGS. 3b and 3c). These percentages are similar to the percentages of patients exhibiting an improvement in symptoms following Blautix treatment or administration of placebo.

Figure 6A:
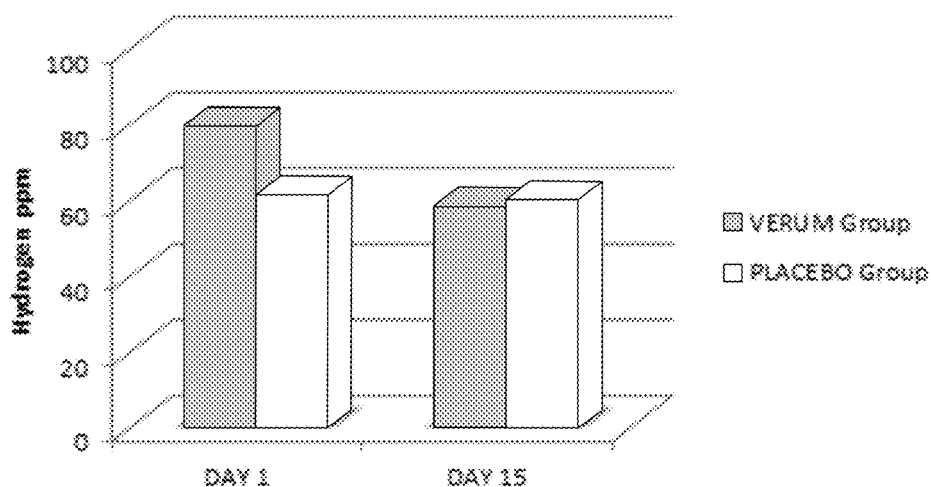
FIG. 6a: Graphs comparing the mean hydrogen breath test results from day 1 and day 15 for the Bautix treatment group (*Verum*) and placebo group for uncorrected hydrogen.
Figure 6B:
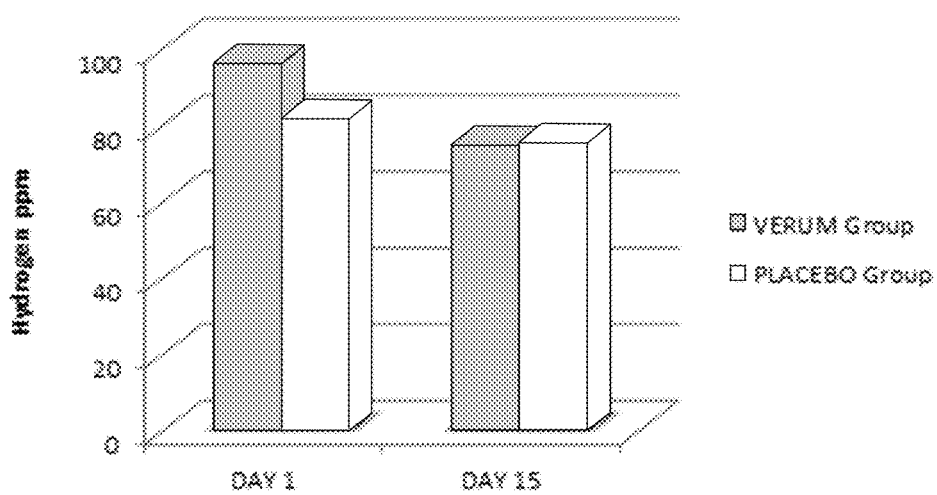
FIG. 6b: Graphs comparing the mean hydrogen breath test results from day 1 and day 15 for the Bautix treatment group (*Verum*) and placebo group for corrected hydrogen (FIG. 6a: uncorrected hydrogen.

FIG. 4 shows the uncorrected and corrected hydrogen results for the Blautix (*Verum*) treatment group together with a statistical analysis of the results. The mean values for both uncorrected and corrected $H_2$ were found to differ between day 1 and day 15. After 13.5 days of treatment, a statistically significant ($p<0.05$) decrease of $H_2$ in Cmax breath test was detected after lactulose stimulation. In contrast, for the placebo group, the mean was found to be equivalent for day 1 and day 15 ($p>0.05$) (FIG. 5). Thus, the mean for the treatment group (also referred to as the VERUM group), decreases between day 1 and day 15 whereas the mean for the placebo group is equivalent between day 1 and day 15 for both the uncorrected hydrogen results and the corrected hydrogen results (FIGS. 6A and 6B).

Example 3—Stability Testing

A composition described herein containing at least one bacterial strain described herein is stored in a sealed container at 25° C. or 4° C. and the container is placed in an atmosphere having 30%, 40%, 50%, 60%, 70%, 75%, 80%, 90% or 95% relative humidity. After 1 month, 2 months, 3 months, 6 months, 1 year, 1.5 years, 2 years, 2.5 years or 3 years, at least 50%, 60%, 70%, 80% or 90% of the bacterial strain shall remain as measured in colony forming units determined by standard protocols.

Sequences

```
(Blautia stercoris strain GAM6-1 16S ribosomal RNA gene,
partial sequence - HM626177)
                                                       SEQ ID NO: 1
       1   tgcaagtcga gcgaagcgct tacgacagaa ccttcggggg aagatgtaag ggactgagcg 61   gcggacgggt gagtaacgcg tgggtaacct gcctcataca ggggataaac agttggaaac 121   ggctgctaat accgcataag cgcacggtat cgcatgatac agtgtgaaaa actccggtgg 181   tatgagatgg acccgcgtct gattagctag ttggaggggt aacggcccac caaggcgacg 241   atcagtagcc ggcctgagag ggtgaacggc cacattggga ctgagacacg gcccagactc 301   ctacgggagg cagcagtggg gaatattgca caatggggga aaccctgatg cagcgacgcc 361   gcgtgaagga agaagtatct cggtatgtaa acttctatca gcagggaaga aaatgacggt 421   acctgactaa gaagccccgg ctaactacgt gccagcagcc gcggtaatac gtaggggca 481   agcgttatcc ggatttactg ggtgtaaagg gagcgtagac ggaagagcaa gtctgatgtg 541   aaaggctggg gcttaaccccc aggactgcat tggaaactgt ttttcttgag tgccggagag 601   gtaagcggaa ttcctagtgt agcggtgaaa tgcgtagata ttaggaggaa caccagtggc 661   gaaggcggct tactggacgg taactgacgt tgaggctcga aagcgtgggg agcaaacagg 721   attagatacc ctggtagtcc acgccgtaaa cgatgaatac taggtgttgg ggagcaaagc 781   tcttcggtgc cgcagcaaac gcaataagta ttccacctgg ggagtacgtt cgcaagaatg 841   aaactcaaag gaattgacgg ggacccgcac aagcggtgga gcatgtggtt taattcgaag 901   caacgcgaag aaccttacca agtcttgaca tcgatctgac cggttcgtaa tggaaccttt 961   ccttcgggac agagaagaca ggtggtgcat ggttgtcgtc agctcgtgtc gtgagatgtt 1021   gggttaagtc ccgcaacgag cgcaacccct atcctcagta gccagcaggt gaagctgggc 1081   actctgtgga gactgccagg gataacctgg aggaaggcgg ggacgacgtc aaatcatcat 1141   gccccttatg atttgggcta cacacgtgct acaatggcgt aaacaaaggg aagcgagccc 1201   gcgagggga gcaaatccca aaaataacgt cccagttcgg actgcagtct gcaactcgac 1261   tgcacgaagc tggaatcgct agtaatcgcg aatcagaatg tcgcggtgaa tacgttcccg 1321   ggtcttgtac acaccgcccg tcacaccatg ggagtcagta acgcccgaag tc (Blautia wexlerae strain WAL 14507 16S ribosomal RNA gene,
partial sequence - EF036467)
                                                       SEQ ID NO: 2
       1   caagtcgaac gggaattant ttattgaaac ttcggtcgat ttaatttaat tctagtggcg 61   gacgggtgag taacgcgtgg gtaacctgcc ttatacaggg ggataacagt cagaaatggc 121   tgctaatacc gcataagcgc acagagctgc atggctcagt gtgaaaaact ccggtggtat 181   aagatggacc cgcgttggat tagcttgttg gtgggggtaac ggcccaccaa ggcgacgatc
```

-continued

```
 241 catagccggc tgagagggt gaacggccac attgggactg agacacggcc cagactccta
 301 cgggaggcag cagtggggaa tattgcacaa tgggggaaac cctgatgcag cgacgccgcg
 361 tgaaggaaga agtatctcgg tatgtaaact tctatcagca gggaagatag tgacggtacc
 421 tgactaagaa gccccggcta actacgtgcc agcagccgcg gtaatacgta gggggcaagc
 481 gttatccgga tttactgggt gtaaagggag cgtagacggt gtggcaagtc tgatgtgaaa
 541 ggcatgggct caacctgtgg actgcattgg aaactgtcat acttgagtgc cggaggggta
 601 agcggaattc ctagtgtagc ggtgaaatgc gtagatatta ggaggaacac cagtggcgaa
 661 ggcggcttac tggacggtaa ctgacgttga ggctcgaaag cgtggggagc aaacaggatt
 721 agataccctg gtagtccacg ccgtaaacga tgaataacta ggtgtcgggt ggcaaagcca
 781 ttcggtgccg tcgcaaacgc agtaagtatt ccacctgggg agtacgttcg caagaatgaa
 841 actcaaagga attgacgggg acccgcacaa gcggtggagc atgtggttta attcgaagca
 901 acgcgaagaa ccttaccaag tcttgacatc cgcctgaccg atccttaacc ggatctttcc
 961 ttcgggacag gcgagacagg tggtgcatgg ttgtcgtcag ctcgtgtcgt gagatgttgg
1021 gttaagtccc gcaacgagcg caaccccctat cctcagtagc cagcatttaa ggtgggcact
1081 ctggggagac tgccagggat aacctggagg aaggcgggga tgacgtcaaa tcatcatgcc
1141 ccttatgatt tgggctacac acgtgctaca atggcgtaaa caaagggaag cgagattgtg
1201 agatggagca aatcccaaaa ataacgtccc agttcggact gtagtctgca acccgactac
1261 acgaagctgg aatcgctagt aatcgcggat cagaatgccg cggtgaatac gttcccgggt
1321 cttgtacaca ccgcccgtca ccatgggag tcagtaacg cccgaagtca gtgacctaac
1381 tgcaaagaag gagctgccga aggcgggacc gatgactggg gtgaagtcgt aacaaggt
```

(consensus 16S rRNA sequence for Blautia stercoris strain 830)

SEQ ID NO: 3

TTTKGTCTGGCTCAGGATGAACGCTGGCGGCGTGCTTAACACATGCAAGT
CGAGCGAAGCGCTTACGACAGAACCTTCGGGGAAGATGTAAGGGACTGA
GCGGCGGACGGGTGAGTAACGCGTGGGTAACCTGCCTCATACAGGGGAT
AACAGTTGGAAACGGCTGCTAATACCGCATAAGCGCACAGTATCGCATGA
TACAGTGTGAAAAACTCCGGTGGTATGAGATGGACCCGCGTCTGATTAGC
TAGTTGGAGGGGTAACGGCCCACCAAGGCGACGATCAGTAGCCGGCCTGA
GAGGGTGAACGCCACATTGGGACTGAGACACGGCCCAGACTCCTACGGG
AGGCAGCAGTGGGGAATATTGCACAATGGGGGAAACCCTGATGCAGCGAC
GCCGCGTGAAGGAAGAAGTATCTCGGTATGTAAACTTCTATCAGCAGGGA
AGAAAATGACGGTACCTGACTAAGAAGCCCCGGCTAACTACGTGCCAGCA
GCCGCGGTAATACGTAGGGGGCAAGCGTTATCCGGATTTACTGGGTGTAA
AGGGAGCGTAGACGGAAGAGCAAGTCTGATGTGAAAGGCTGGGGCTTAAC
CCCAGGACTGCATTGGAAACTGTTTTTCTTGAGTGCCGGAGAGGTAAGCG
GAATTCCTAGTGTAGCGGTGAAATGCGTAGATATTAGGAGGAACACCAGT
GGCGAAGGCGGCTTACTGGACGGTAACTGACGTTGAGGCTCGAAAGCGTG
GGGAGCAAACAGGATTAGATACCCTGGTAGTCCACGCCGTAAACGATGAA
TACTAGGTGTTGGGGAGCAAAGCTCTTCGGTGCCGCAGCAAACGCAATAA
GTATTCCACCTGGGGAGTACGTTCGCAAGAATGAAACTCAAAGGAATTGA
CGGGGACCCGCACAAGCGGTGGAGCATGTGGTTTATTCGAAGCAACGCGA
AGAACCTTACCAAGTCTTGACATCGATCTGACCGGTTCGTAATGGAACCT
TTCCTTCGGGACAGAGAAGACAGGTGGTGCATGGTTGTCGTCAGCTCGTG
TCGTGAGATGTTGGGTTAAGTCCCGCAACGAGCGCAACCCCTATCGTCAG
TAGCCAGCAGGTAAAGCTGGGCACTCTGAGGAGACTGCCAGGGATAACCT
GGAGGAAGGCGGGGACGACGTCAAATCATCATGCCCCTTATGATTTGGGC
TACACACGTGCTACAATGGCGTAAACAAAGGGAAGCGAGCCCGCGAGGGG
GAGCAAATCCCAAAAATAACGTCCCAGTTCGGACTGCAGTCTGCAACTCG
ACTGCACGAAGCTGGAATCGCTAGTAATCGCGAATCAGAATGTCGCGGTG
AATACGTTCCCGGGTCTTGTACACACCGCCCGTCACACCATGGGAGTCAG
TAACGCCCGAAGTCAGTGACCCAACCTTAGGGAGGGAGCTGCCGAAGGCG
GGATTGATAACTGGGGTGAAGTCTAGGGGGT (consensus 16S rRNA sequence for Blautia wexlerae strain MRX008)

SEQ ID NO: 4

TTCATTGAGACTTCGGTGGATTTAGATTCTATTTCTAGTGGCGGACGGGT
GAGTAACGCGTGGGTAACCTGCCTTATACAGGGGATAACAGTCAGAAAT
GGCTGCTAATACCGCATAAGCGCACAGAGCTGCATGGCTCAGTGTGAAAA
ACTCCGGTGGTATAAGATGGACCCGCGTTGGATTAGCTTGTTGGTGGGGT
AACGGCCCACCAAGGCGACGATCCATAGCCGGCCTGAGAGGGTGAACGGC

-continued

```
CACATTGGGACTGAGACACGGCCCAGACTCCTACGGGAGGCAGCAGTGGG
GAATATTGCACAATGGGGGAAACCCTGATGCAGCGACGCCGCGTGAAGGA
AGAAGTATCTCGGTATGTAAACTTCTATCAGCAGGGAAGATAGTGACGGT
ACCTGACTAAGAAGCCCCGGCTAACTACGTGCCAGCAGCCGCGGTAATAC
GTAGGGGGCAAGCGTTATCCGGATTTACTGGGTGTAAAGGGAGCGTAGAC
GGTGTGGCAAGTCTGATGTGAAAGGCATGGGCTCAACCTGTGGACTGCAT
TGGAAACTGTCATACTTGAGTGCCGGAGGGGTAAGCGGAATTCCTAGTGT
AGCGGTGAAATGCGTAGATATTAGGAGGAACACCAGTGGCGAAGGCGGCT
TACTGGACGGTAACTGACGTTGAGGCTCGAAAGCGTGGGGAGCAAACAGG
ATTAGATACCCTGGTAGTCCACGCCGTAAACGATGAATACTAGGTGTCNG
GGGAGCATGGCTCTTCGGTGCCGTCGCAAACGCAGTAAGTATTCCACCTG
GGGAGTACGTTCGCAAGAATGAAACTCAAAGGAATTGACGGGGACCCGCA
```

```
CAAGCGGTGGAGCATGTGGTTTAATTCGAAGCAACGCGAAGAACCTTACC
AAGTCTTGACATCCGCCTGACCGATCCTTAACCGGATCTTTCCTTCGGGA
CAGGCGAGACAGGTGGTGCATGGTTGTCGTCAGCTCGTGTCGTGAGATGT
TGGGTTAAGTCCCGCAACGAGCGCAACCCCTATCCTCAGTAGCCAGCATT
TAAGGTGGGCACTCTGGGGAGACTGCCAGGGATAACCTGGAGGAAGGCGG
GGATGACGTCAAATCATCATGCCCCTTATGATTTGGGCTACACACGTGCT
ACAATGGCGTAAACAAAGGGAAGCGAGATCGTGAGATGGAGCAAATCCCA
AAAATAACGTCCCAGTTCGGACTGTAGTCTGCAACCCGACTACACGAAGC
TGGAATCGCTAGTAATCGCGGATCAGAATGCCGCGGTGAATACGTTCCCG
GTCTTGTACACACCGCCCGTCACACCATGGGAGTCAGTAACGCCCGAAG
TCAGTGACCTAACTGCAAAGAAGGAGCTGCCGAA
```

(*Blautia hydrogenotrophica* strain S5a36 16S ribosomal RNA gene, partial sequence- X95624.1)

SEQ ID NO: 5

```
   1  gatgaacgct ggcggcgtgc ttaacacatg caagtcgaac gaagcgatag agaacggaga
  61  tttcggttga agtttctat tgactgagtg gcggacgggt gagtaacgcg tgggtaacct
 121  gccctataca gggggataac agttagaaat gactgctaat accgcataag cgcacagctt
 181  cgcatgaagc ggtgtgaaaa actgaggtgg tataggatgg acccgcgttg gattagctag
 241  ttggtgaggt aacggcccac caaggcgacg atccatagcc ggcctgagag ggtgaacggc
 301  cacattggga ctgagacacg gcccaaactc ctacgggagg cagcagtggg gaatattgca
 361  caatggggga accctgatg cagcgacgcc gcgtgaagga agaagtatct cggtatgtaa
 421  acttctatca gcagggaaga agtgacggt acctgactaa gaagccccgg ctaattacgt
 481  gccagcagcc gcggtaatac gtaaggggca agcgttatcc ggatttactg ggtgtaaagg
 541  gagcgtagac ggtttggcaa gtctgatgtg aaaggcatgg gctcaacctg tggactgcat
 601  tggaaactgt cagacttgag tgccggagag gcaagcggaa ttcctagtgt agcggtgaaa
 661  tgcgtagata ttaggaggaa caccagtggc gaaggcggcc tgctggacgg taactgacgt
 721  tgaggctcga aagcgtgggg agcaaacagg attagatacc ctggtagtcc acgctgtaaa
 781  cgatgaatac taggtgtcgg gtggcaaagc cattcggtgc cgcagcaaac gcaataagta
 841  ttcccacctg gggagtacgt tcgcaagaat gaaactcaaa ggaattgacg ggacccgca
 901  caagcggtgg agcatgtggt ttaattcgaa gcaacgcgaa gaaccttacc aaatcttgac
 961  atccctctga ccgggaagta atgttccctt ttcttcggaa cagaggagac aggtggtgca
1021  tggttgtcg tcagctcgtg tcgtgagatg ttgggttaagt cccgcaacg agcgcaaccct
1081  tattcttag tagccagcag gtagagctgg gcactctaggg agactgcca gggataacctg
1141  gaggaaggt ggggatgacg tcaaatcatc atgccccttat gatttgggc tacacacgtgc
1201  tacaatggc gtaaacaaag ggaagcgaag gggtgacctgg agcaaatct caaaaataacg
1261  tctcagttc ggattgtagt ctgcaactcg actacatgaag ctggaatc ctagtaatcgc
1321  gaatcagaa tgtcgcggtg aatacgttcc gggtcttgta cacaccgcc cgtcacaccat
1381  gggagtcag taacgcccga agtcagtgac ccaaccnaaag gagggagct gccgaaggtgg
1441  gactgataa ctggggtga
```

REFERENCES

[1] Spor et al. (2011) *Nat Rev Microbiol.* 9(4):279-90.
[2] Eckburg et al. (2005) *Science.* 10; 308(5728):1635-8.
[3] Tap et al. (2009) *Environ Microbiol,* 11(10):2574-84
[4] Macpherson et al. (2001) *Microbes Infect.* 3(12):1021-35
[5] Macpherson et al. (2002) *Cell Mol Life Sci.* 59(12):2088-96.
[6] Mazmanian et al. (2005) *Cell* 15; 122(1):107-18.
[7] Frank et al. (2007) *PNAS* 104(34):13780-5.
[8] Scanlan et al. (2006) *J Clin Microbiol.* 44(11):3980-8.
[9] Kang et al. (2010) *Inflamm Bowel Dis.* 16(12):2034-42.
[10] Machiels et al. (2013) *Gut.* 63(8):1275-83.
[11] Lopetuso et al. (2013), Gut Pathogens, 5: 23
[12] WO 2013/050792
[13] WO 03/046580
[14] WO 2013/008039
[15] WO 2014/167338
[16] Lee and Lee (2014) *World J Gastroenterol.* 20(27): 8886-8897.
[17] Liu et al. (2008) *Int J Syst Evol Microbiol* 58, 1896-1902.
[18] Bernalier et al. (1996) *Arch. Microbiol.* 166 (3), 176-183.
[19] Park et al. (2012) *Int J Syst Evol Microbiol.* 62(Pt 4):776-9.
[20] Masco et al. (2003) *Systematic and Applied Microbiology,* 26:557-563.
[21] Srâtková et al. (2011) *J. Microbiol. Methods,* 87(1): 10-6.
[22] Darfeuille-Michaud et al. (2004) *Gastroenterology* 127 (2):412-21.
[23] Strus et al. (2015) Cent Eur J Immunol. 40(4):420-30.
[24] Petersen et al. (2015) *Scand J Gastroenterol.;* 50(10): 1199-207.
[25] Miyamoto-Shinohara et al. (2008) *J. Gen. Appl. Microbiol.,* 54, 9-24.
[26] Cryopreservation and Freeze-Drying Protocols, ed. by Day and McLellan, Humana Press.
[27] Leslie et al. (1995) *Appl. Environ. Microbiol.* 61, 3592-3597.
[28] Mitropoulou et al. (2013) *J Nutr Metab.* (2013) 716861.
[29] Kailasapathy et al. (2002) *Curr Issues Intest Microbiol.* 3(2):39-48.
[30] Handbook of Pharmaceutical Excipients, 2nd Edition, (1994), Edited by A Wade and PJ Weller
[31] Remington's Pharmaceutical Sciences, Mack Publishing Co. (A. R. Gennaro edit. 1985)
[32] US 2016/0067188
[33] *Handbook of Microbiological Media, Fourth Edition* (2010) Ronald Atlas, CRC Press.
[34] *Maintaining Cultures for Biotechnology and Industry* (1996) Jennie C. Hunter-Cevera, Academic Press
[35] Strobel (2009) *Methods Mol Biol.* 581:247-61.
[36] Gennaro (2000) *Remington: The Science and Practice of Pharmacy.* 20th edition, ISBN: 0683306472.
[37] *Molecular Biology Techniques: An Intensive Laboratory Course,* (Ream et al., eds., 1998, Academic Press).
[38] *Methods In Enzymology* (S. Colowick and N. Kaplan, eds., Academic Press, Inc.)
[39] *Handbook of Experimental Immunology,* Vols. I-IV (D. M. Weir and C. C. Blackwell, eds, 1986, Blackwell Scientific Publications)
[40] Sambrook et al. (2001) *Molecular Cloning: A Laboratory Manual,* 3rd edition (Cold Spring Harbor Laboratory Press).
[41] *Handbook of Surface and Colloidal Chemistry* (Birdi, K. S. ed., CRC Press, 1997)
[42] Ausubel et al. (eds) (2002) *Short protocols in molecular biology,* 5th edition (Current Protocols).
[43] *PCR (Introduction to Biotechniques Series),* 2nd ed. (Newton & Graham eds., 1997, Springer Verlag)
[44] *Current Protocols in Molecular Biology* (F. M. Ausubel et al., eds., 1987) Supplement 30
[45] Smith & Waterman (1981) *Adv. Appl. Math.* 2: 482-489.

The invention claimed is:

1. A method of treating diarrhea, constipation, or diarrhea and constipation in a subject in need thereof, comprising administering to the subject a pharmaceutical composition comprising:
a bacteria strain of *Blautia hydrogenotrophica* sufficient to treat the diarrhea, constipation, or diarrhea and constipation in the subject; and
a pharmaceutically acceptable excipient, diluent, or carrier,
wherein the bacteria strain comprises a 16S rRNA gene sequence of SEQ ID NO: 5,
and
wherein the administering results in a reduction in the diarrhea, constipation, or diarrhea and constipation in the subject.

2. The method of claim 1, wherein the bacteria strain is active.

3. The method of claim 1, wherein the pharmaceutical composition is encapsulated.

4. The method of claim 1, wherein the pharmaceutical composition is lyophilized.

5. The method of claim 1, wherein the pharmaceutical composition is formulated for oral delivery.

6. The method of claim 5, wherein the pharmaceutical composition is enterically coated.

7. The method of claim 1, wherein the pharmaceutical composition comprises from about $1\times10^3$ to about $1\times10^{11}$ colony forming units (CFU)/g of the bacteria strain with respect to a total weight of the pharmaceutical composition.

8. The method of claim 1, wherein the subject has diarrhea and constipation.

9. The method of claim 1, wherein the pharmaceutical composition comprises an amount sufficient to reduce an amount of hydrogen in the breath of the subject as determined by an administration of lactulose followed by a hydrogen breath analysis.

10. The method of claim 1, wherein the administering comprises providing one or more doses of 1 g, 3 g, 5 g or 10 g of the pharmaceutical composition.

11. The method of claim 1, wherein at least 50% of the bacteria strain as measured by an amount of colony forming units (CFU) remains viable after about 1 year of storage when the pharmaceutical composition is stored in a closed container at 25° C. at 95% relative humidity.

* * * * *

SEQUENCE LISTING

```
<160> NUMBER OF SEQ ID NOS: 5

<210> SEQ ID NO 1
<211> LENGTH: 1372
<212> TYPE: DNA
<213> ORGANISM: Blautia stercoris

<400> SEQUENCE: 1
tgcaagtcga gcgaagcgct tacgacagaa ccttcggggg aagatgtaag ggactgagcg      60
gcggacgggt gagtaacgcg tgggtaacct gcctcataca gggggataac agttggaaac     120
ggctgctaat accgcataag cgcacggtat cgcatgatac agtgtgaaaa actccggtgg     180
tatgagatgg acccgcgtct gattagctag ttggaggggt aacggcccac caaggcgacg     240
atcagtagcc ggcctgagag ggtgaacggc cacattggga ctgagacacg gcccagactc     300
ctacgggagg cagcagtggg gaatattgca caatggggga aaccctgatg cagcgacgcc     360
gcgtgaagga agaagtatct cggtatgtaa acttctatca gcaggaaga aaatgacggt     420 acctgactaa gaagccccgg ctaactacgt gccagcagcc gcggtaatac gtaggggca     480 agcgttatcc ggatttactg ggtgtaaagg gagcgtagac ggaagagcaa gtctgatgtg     540
aaaggctggg gcttaacccc aggactgcat tggaaactgt ttttcttgag tgccggagag     600
gtaagcggaa ttcctagtgt agcggtgaaa tgcgtagata ttaggaggaa caccagtggc     660
```

```
gaaggcggct tactggacgg taactgacgt tgaggctcga aagcgtgggg agcaaacagg      720
attagatacc ctggtagtcc acgccgtaaa cgatgaatac taggtgttgg ggagcaaagc      780
tcttcggtgc cgcagcaaac gcaataagta ttccacctgg ggagtacgtt cgcaagaatg      840
aaactcaaag gaattgacgg ggacccgcac aagcggtgga gcatgtggtt taattcgaag      900
caacgcgaag aaccttacca agtcttgaca tcgatctgac cggttcgtaa tggaaccttt      960
ccttcgggac agagaagaca ggtggtgcat ggttgtcgtc agctcgtgtc gtgagatgtt     1020
gggttaagtc ccgcaacgag cgcaacccct atcctcagta gccagcaggt gaagctgggc     1080
actctgtgga gactgccagg gataacctgg aggaaggcgg ggacgacgtc aaatcatcat     1140
gccccttatg atttgggcta cacacgtgct acaatggcgt aaacaaaggg aagcgagccc     1200
gcgaggggga gcaaatccca aaaataacgt cccagttcgg actgcagtct gcaactcgac     1260
tgcacgaagc tggaatcgct agtaatcgcg aatcagaatg tcgcggtgaa tacgttcccg     1320
ggtcttgtac acaccgcccg tcacaccatg ggagtcagta acgcccgaag tc             1372
```

<210> SEQ ID NO 2
<211> LENGTH: 1438
<212> TYPE: DNA
<213> ORGANISM: Blautia wexlerae
<220> FEATURE:
<221> NAME/KEY: modified base
<222> LOCATION: 19
<223> OTHER INFORMATION: 'n' is a, c, g or t

<400> SEQUENCE: 2

```
caagtcgaac gggaattant ttattgaaac ttcggtcgat ttaatttaat tctagtggcg       60
gacgggtgag taacgcgtgg gtaacctgcc ttatacaggg ggataacagt cagaaatggc      120
tgctaatacc gcataagcgc acagagctgc atggctcagt gtgaaaaact ccggtggtat      180
aagatggacc cgcgttggat tagcttgttg gtggggtaac ggcccaccaa ggcgacgatc      240
catagccggc ctgagagggt gaacggccac attgggactg agacacggcc cagactccta      300
cgggaggcag cagtggggaa tattgcacaa tgggggaaac cctgatgcag cgacgccgcg      360
tgaaggaaga agtatctcgg tatgtaaact tctatcagca gggaagatag tgacggtacc      420
tgactaagaa gccccggcta actacgtgcc agcagccgcg gtaatacgta ggggcaagc      480 gttatccgga tttactgggt gtaaagggag cgtagacggt gtggcaagtc tgatgtgaaa      540
ggcatgggct caacctgtgg actgcattgg aaactgtcat acttgagtgc cggagggta      600 agcggaattc ctagtgtagc ggtgaaatgc gtagatatta ggaggaacac cagtggcgaa      660
ggcggcttac tggacggtaa ctgacgttga ggctcgaaag cgtgggagc aaacaggatt      720 agataccctg gtagtccacg ccgtaaacga tgaataacta ggtgtcgggt ggcaaagcca      780
ttcggtgccg tcgcaaacgc agtaagtatt ccacctgggg agtacgttcg caagaatgaa      840
actcaaagga attgacgggg acccgcacaa gcggtggagc atgtggttta attcgaagca      900
acgcgaagaa ccttaccaag tcttgacatc cgcctgaccg atccttaacc ggatctttcc     960
ttcgggacag gcgagacagg tggtgcatgg ttgtcgtcag ctcgtgtcgt gagatgttgg     1020
gttaagtccc gcaacgagcg caaccccctat cctcagtagc cagcatttaa ggtgggcact     1080
ctggggagac tgccagggat aacctggagg aaggcgggga tgacgtcaaa tcatcatgcc     1140
ccttatgatt tgggctacac acgtgctaca atgcgtaaaa caagggaag cgagattgtg     1200 agatggcaga aatcccaaaa ataacgtccc agttcggact gtagtctgca acccgactac     1260
acgaagctgg aatcgctagt aatcgcggat cagaatgccg cggtgaatac gttcccgggt     1320
```

```
cttgtacaca ccgcccgtca caccatggga gtcagtaacg cccgaagtca gtgacctaac      1380
tgcaaagaag gagctgccga aggcgggacc gatgactggg gtgaagtcgt aacaaggt        1438

<210> SEQ ID NO 3
<211> LENGTH: 1481
<212> TYPE: DNA
<213> ORGANISM: Blautia stercoris
<220> FEATURE:
<221> NAME/KEY: modified_base
<222> LOCATION: 4
<223> OTHER INFORMATION: 'k' is g or t

<400> SEQUENCE: 3
tttkgtctgg ctcaggatga acgctggcgg cgtgcttaac acatgcaagt cgagcgaagc      60
gcttacgaca gaaccttcgg gggaagatgt aagggactga gcggcggacg ggtgagtaac      120
gcgtgggtaa cctgcctcat acagggggat aacagttgga aacggctgct aataccgcat      180
aagcgcacag tatcgcatga tacagtgtga aaaactccgg tggtatgaga tggacccgcg      240
tctgattagc tagttggagg ggtaacggcc caccaaggcg acgatcagta gccgccctga      300
gagggtgaac ggccacattg gactgagaca cggcccaga ctcctacggg aggcagcagt       360
ggggaatatt gcacaatggg ggaaaccctg atgcagcgac gccgcgtgaa ggaagaagta      420
tctcggtatg taaacttcta tcagcaggga agaaaatgac ggtacctgac taagaagccc      480
cggctaacta cgtgccagca gccgcggtaa tacgtagggg gcaagcgtta tccggattta      540
ctgggtgtaa agggagcgta gacggaagag caagtctgat gtgaaaggct ggggcttaac      600
cccaggactg cattggaaac tgttttttctt gagtgccgga gaggtaagcg gaattcctag      660
tgtagcggtg aaatgcgtag atattaggag gaacaccagt ggcgaaggcg gcttactgga      720
cggtaactga cgttgaggct cgaaagcgtg gggagcaaac aggattagat accctggtag      780
tccacgccgt aaacgatgaa tactaggtgt tggggagcaa agctcttcgg tgccgcagca      840
aacgcaataa gtattccacc tggggagtac gttcgcaaga atgaaactca aaggaattga      900
cggggacccg cacaagcggt ggagcatgtg gtttaattcga agcaacgcga agaaccttac      960
caagtcttga catcgatctg accggttcgt aatggaacct ttccttcggg acagagaaga     1020
caggtggtgc atggttgtcg tcagctcgtg tcgtgagatg ttgggttaag tcccgcaacg     1080
agcgcaaccc ctatcgtcag tagccagcag gtaaagctgg gcactctgag gagactgcca     1140
gggataacct ggaggaaggc ggggacgacg tcaaatcatc atgccccctta tgatttgggc    1200 tacacacgtg ctacaatggc gtaaacaaag ggaagcgagc ccgcgagggg gagcaaatcc     1260
caaaaataac gtcccagttc ggactgcagt ctgcaactcg actgcacgaa gctggaatcg     1320
ctagtaatcg cgaatcagaa tgtcgcggtg aatacgttcc cggtcttgt acacaccgcc      1380 cgtcacacca tgggagtcag taacgcccga agtcagtgac ccaaccttag ggagggagct     1440
gccgaaggcg ggattgataa ctggggtgaa gtctaggggg t                         1481

<210> SEQ ID NO 4
<211> LENGTH: 1384
<212> TYPE: DNA
<213> ORGANISM: Blautia wexlerae
<220> FEATURE:
<221> NAME/KEY: modified_base
<222> LOCATION: 749
<223> OTHER INFORMATION: 'n' is a, c, g or t
```

<400> SEQUENCE: 4

```
ttcattgaga cttcggtgga tttagattct atttctagtg gcggacgggt gagtaacgcg      60
tgggtaacct gccttataca gggggataac agtcagaaat ggctgctaat accgcataag     120
cgcacagagc tgcatggctc agtgtgaaaa actccggtgg tataagatgg acccgcgttg     180
gattagcttg ttggtggggt aacggcccac caaggcgacg atccatagcc ggcctgagag     240
ggtgaacggc cacattggga ctgagacacg gcccagactc ctacgggagg cagcagtggg     300
gaatattgca caatggggga aaccctgatg cagcgacgcc gcgtgaagga agaagtatct     360
cggtatgtaa acttctatca gcagggaaga tagtgacggt acctgactaa gaagccccgg     420
ctaactacgt gccagcagcc gcggtaatac gtaggggggca agcgttatcc ggatttactg     480
ggtgtaaagg gagcgtagac ggtgtggcaa gtctgatgtg aaaggcatgg gctcaacctg     540
tggactgcat tggaaactgt catacttgag tgccggaggg gtaagcggaa ttcctagtgt     600
agcggtgaaa tgcgtagata ttaggaggaa caccagtggc gaaggcggct tactggacgg     660
taactgacgt tgaggctcga aagcgtgggg agcaaacagg attagatacc ctggtagtcc     720
acgccgtaaa cgatgaatac taggtgtcng gggagcatgg ctcttcggtg ccgtcgcaaa     780
cgcagtaagt attccacctg gggagtacgt tcgcaagaat gaaactcaaa ggaattgacg     840
gggacccgca caagcggtgg agcatgtggt ttaattcgaa gcaacgcgaa gaaccttacc     900
aagtcttgac atccgcctga ccgatcctta accggatctt tccttcggga caggcgagac     960
aggtggtgca tggttgtcgt cagctcgtgt cgtgagatgt tgggttaagt cccgcaacga    1020
gcgcaacccc tatcctcagt agccagcatt aaggtgggc actctgggga gactgccagg    1080
gataacctgg aggaaggcgg ggatgacgtc aaatcatcat gccccttatg atttgggcta    1140
cacacgtgct acaatggcgt aaacaaaggg aagcgagatc gtgagatgga gcaaatccca    1200
aaaataacgt cccagttcgg actgtagtct gcaacccgac tacacgaagc tggaatcgct    1260
agtaatcgcg gatcagaatg ccgcggtgaa tacgttcccg ggtcttgtac acaccgcccg    1320
tcacaccatg ggagtcagta acgcccgaag tcagtgacct aactgcaaag aaggagctgc    1380
cgaa                                                                 1384
```

<210> SEQ ID NO 5
<211> LENGTH: 1458
<212> TYPE: DNA
<213> ORGANISM: Blautia hydrogenotrophica
<220> FEATURE:
<221> NAME/KEY: modified base
<222> LOCATION: 1416
<223> OTHER INFORMATION: 'n' is a, c, g or t

<400> SEQUENCE: 5

```
gatgaacgct ggcggcgtgc ttaacacatg caagtcgaac gaagcgatag agaacggaga      60
tttcggttga agttttctat tgactgagtg gcggacgggt gagtaacgcg tgggtaacct     120
gccctataca gggggataac agttagaaat gactgctaat accgcataag cgcacagctt     180
cgcatgaagc ggtgtgaaaa actgaggtgg tataggatgg acccgcgttg gattagctag     240
ttggtgaggt aacggcccac caaggcgacg atccatagcc ggcctgagag ggtgaacggc     300
cacattggga ctgagacacg gcccaaactc ctacgggagg cagcagtggg gaatattgca     360
caatggggga aaccctgatg cagcgacgcc gcgtgaagga agaagtatct cggtatgtaa     420
acttctatca gcagggaaga aagtgacggt acctgactaa gaagccccgg ctaattacgt     480
gccagcagcc gcggtaatac gtaggggggca agcgttatcc ggatttactg ggtgtaaagg     540
```

```
gagcgtagac ggtttggcaa gtctgatgtg aaaggcatgg gctcaacctg tggactgcat      600
tggaaactgt cagacttgag tgccggagag gcaagcggaa ttcctagtgt agcggtgaaa      660
tgcgtagata ttaggaggaa caccagtggc gaaggcggcc tgctggacgg taactgacgt      720
tgaggctcga aagcgtgggg agcaaacagg attagatacc ctggtagtcc acgctgtaaa      780
cgatgaatac taggtgtcgg gtggcaaagc cattcggtgc cgcagcaaac gcaataagta      840
ttcccacctg gggagtacgt tcgcaagaat gaaactcaaa ggaattgacg ggacccgca       900 caagcggtgg agcatgtggt ttaattcgaa gcaacgcgaa gaaccttacc aaatcttgac      960
atccctctga ccgggaagta atgttccctt ttcttcggaa cagaggagac aggtggtgca     1020
tggttgtcgt cagctcgtgt cgtgagatgt tgggttaagt cccgcaacga gcgcaaccct     1080
tattcttagt agccagcagg tagagctggg cactctaggg agactgccag ggataacctg     1140
gaggaaggtg gggatgacgt caaatcatca tgccccttat gatttgggct acacacgtgc     1200
tacaatggcg taaacaaagg gaagcgaagg ggtgacctgg agcaaatctc aaaaataacg     1260
tctcagttcg gattgtagtc tgcaactcga ctacatgaag ctggaatcgc tagtaatcgc     1320
gaatcagaat gtcgcggtga atacgttccc gggtcttgta cacaccgccc gtcacaccat     1380
gggagtcagt aacgcccgaa gtcagtgacc caaccnaaag gagggagctg ccgaaggtgg     1440
gactgataac tggggtga                                                   1458
```